(12) United States Patent
Gorski et al.

(10) Patent No.: US 12,144,498 B2
(45) Date of Patent: Nov. 19, 2024

(54) LAPAROSCOPIC SUTURING SYSTEM

(71) Applicant: Applied Medical Resources Corporation, Rancho Santa Margarita, CA (US)

(72) Inventors: Steven Gorski, Costa Mesa, CA (US); Scott V. Taylor, Rancho Santa Margarita, CA (US); Kimball B. McGinley, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 17/854,632

(22) Filed: Jun. 30, 2022

(65) Prior Publication Data

US 2022/0323065 A1 Oct. 13, 2022

Related U.S. Application Data

(60) Continuation of application No. 16/565,065, filed on Sep. 9, 2019, now Pat. No. 11,406,373, which is a
(Continued)

(51) Int. Cl.
*A61B 17/04* (2006.01)
*A61B 17/06* (2006.01)
*A61B 17/062* (2006.01)

(52) U.S. Cl.
CPC .... *A61B 17/0469* (2013.01); *A61B 17/06166* (2013.01); *A61B 17/0625* (2013.01);
(Continued)

(58) Field of Classification Search
CPC .......... A61B 17/0469; A61B 17/06166; A61B 17/0625; A61B 2017/0417;
(Continued)

(56) References Cited

U.S. PATENT DOCUMENTS 2,591,063 A 4/1952 Goldberg
3,311,110 A 3/1967 Singerman et al.
(Continued)

FOREIGN PATENT DOCUMENTS

| EP | 0 903 109 A1 | 3/1999 |
| EP | 2 462 877 A2 | 6/2012 |
| JP | 2000 037391 A | 2/2000 |

OTHER PUBLICATIONS

European Patent Office, The International Search Report and Written Opinion of the International Searching Authority for International Application No. PCT/US2016/051089 titled "Laparoscopic Suturing System", mailed Jan. 23, 2017, 19 pgs.
(Continued)

*Primary Examiner* — Jing Rui Ou
(74) *Attorney, Agent, or Firm* — John F. Heal

(57) ABSTRACT

A laparoscopic suturing device is provided. The suturing device can pass a suturing needle back and forth between jaws of a jaw assembly to suture tissue at a surgical site in a minimally invasive procedure. The jaw assembly can have a pivotable jaw member in each jaw to position the jaw assembly and needle in a low-profile stowed configuration for insertion through a low diameter surgical port. The jaw assembly can be actuated by a handle assembly that provides simultaneous needle passing from a driving jaw to a receiving jaw and latching the needle within the receiving jaw in a single trigger cycle.

13 Claims, 24 Drawing Sheets

Related U.S. Application Data division of application No. 15/261,422, filed on Sep. 9, 2016, now Pat. No. 10,405,851.

(60) Provisional application No. 62/217,502, filed on Sep. 11, 2015.

(52) U.S. Cl.
CPC ............ *A61B 2017/0417* (2013.01); *A61B 2017/06019* (2013.01); *A61B 2017/06033* (2013.01); *A61B 2017/06038* (2013.01); *A61B 2017/06047* (2013.01); *A61B 2017/0609* (2013.01); *A61B 2017/06176* (2013.01)

(58) Field of Classification Search
CPC A61B 2017/06019; A61B 2017/06033; A61B 2017/06038; A61B 2017/06047; A61B 2017/0609; A61B 2017/06176
See application file for complete search history.

(56) References Cited

U.S. PATENT DOCUMENTS

| | | | |
|---|---|---|---|
| 3,842,840 A | 10/1974 | Schweizer | |
| 5,318,577 A | 6/1994 | Li | |
| 5,397,325 A | 3/1995 | Della Badia et al. | |
| 5,431,666 A | 7/1995 | Sauer et al. | |
| 5,454,823 A | 10/1995 | Richardson et al. | |
| 5,478,344 A | 12/1995 | Stone et al. | |
| 5,478,345 A | 12/1995 | Stone et al. | |
| 5,480,406 A | 1/1996 | Nolan et al. | |
| 5,569,301 A * | 10/1996 | Granger | A61B 17/0469 606/224 |
| D384,413 S | 9/1997 | Zlock et al. | |
| 5,674,229 A | 10/1997 | Tovey et al. | |
| 5,674,230 A | 10/1997 | Tovey et al. | |
| 5,814,054 A | 9/1998 | Kortenbach et al. | |
| 5,871,488 A | 2/1999 | Tovey et al. | |
| 5,895,395 A | 4/1999 | Yeung | |
| 6,056,771 A | 5/2000 | Proto | |
| 8,292,906 B2 | 10/2012 | Taylor et al. | |
| 8,460,275 B2 | 6/2013 | Taylor et al. | |
| 8,465,506 B2 | 6/2013 | McLawhorn et al. | |
| 8,490,713 B2 | 7/2013 | Furnish et al. | |
| 8,517,073 B2 | 8/2013 | Bogart et al. | |
| 8,906,043 B2 | 12/2014 | Woodard, Jr. et al. | |
| 2003/0109900 A1* | 6/2003 | Martinek | A61F 2/0811 606/219 |
| 2005/0192633 A1* | 9/2005 | Montpetit | A61B 17/0469 606/232 |
| 2006/0036232 A1* | 2/2006 | Primavera | A61B 17/29 604/411 |
| 2009/0312773 A1* | 12/2009 | Cabrera | A61B 17/0469 606/144 |
| 2010/0010512 A1* | 1/2010 | Taylor | A61B 17/0491 606/144 |
| 2010/0228270 A1 | 9/2010 | Bogart et al. | |
| 2012/0150197 A1 | 6/2012 | Malkowski | |
| 2015/0142018 A1 | 5/2015 | Sniffin et al. | |
| 2015/0209028 A1 | 7/2015 | Sniffin et al. | |

OTHER PUBLICATIONS

The International Bureau of WIPO, International Preliminary Report on Patentability, for International Application No. PCT/US2016/051089, entitled "Laparoscopic Suturing System," dated Mar. 22, 2018, 13 pgs.

* cited by examiner

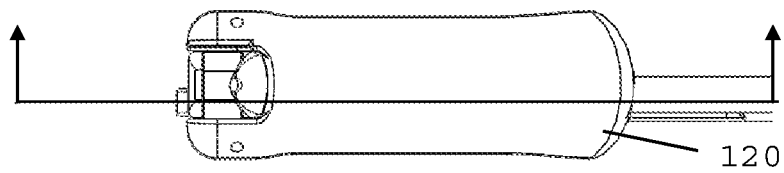
FIG. 13
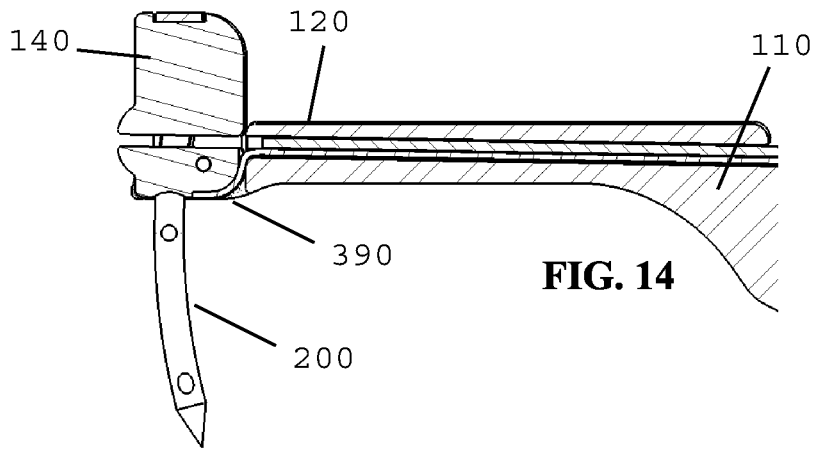
FIG. 14
FIG. 15
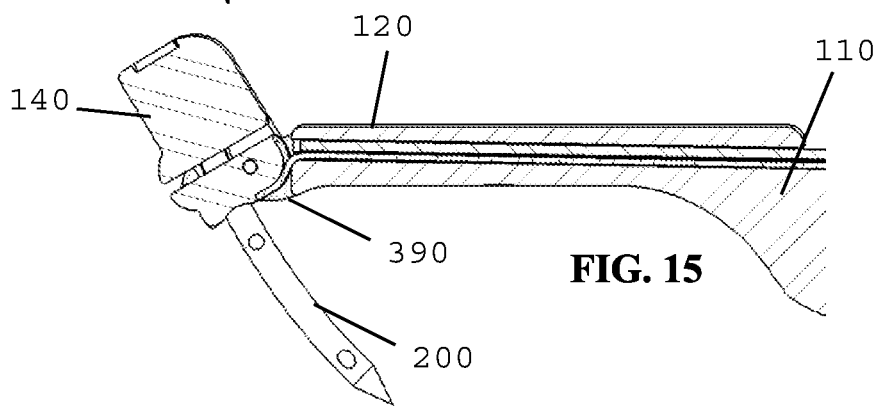
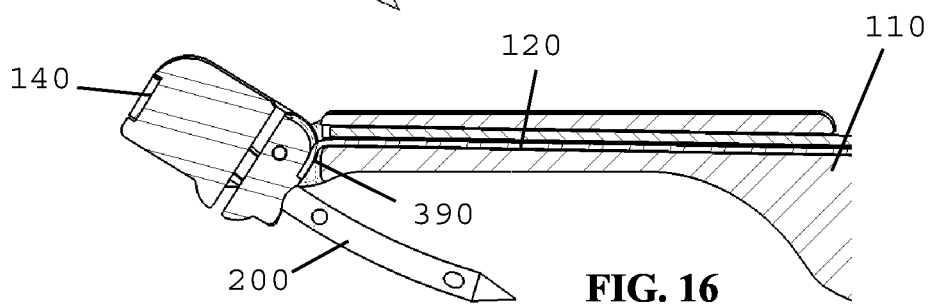
FIG. 16
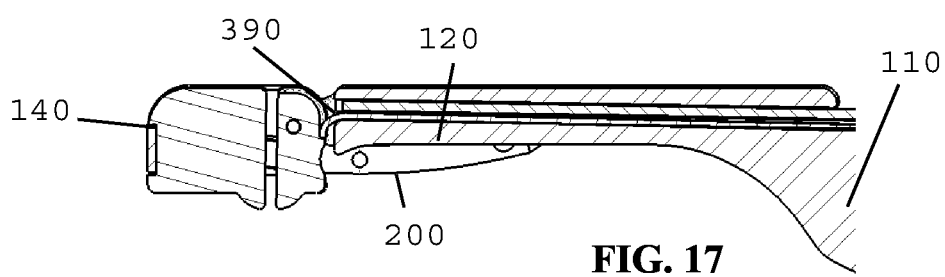
FIG. 17

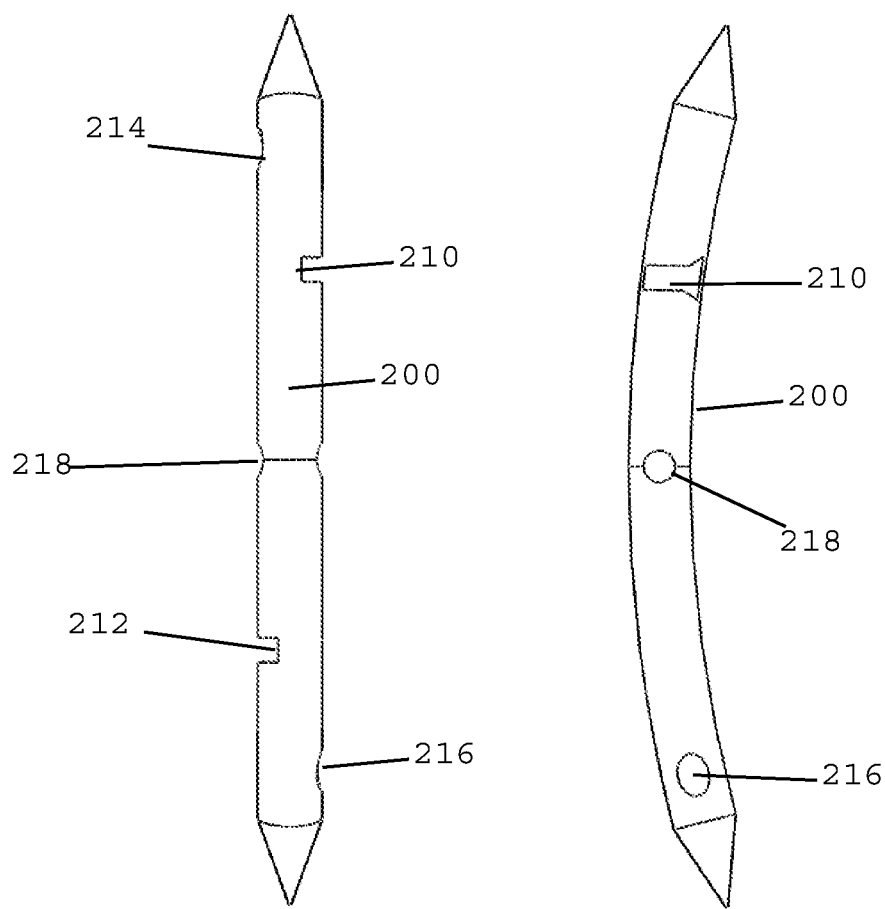
FIG. 28  FIG. 29
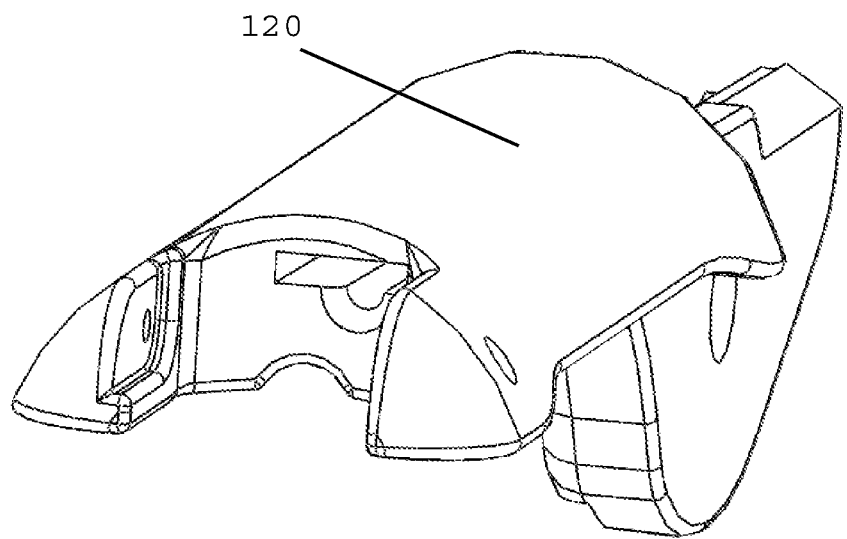
FIG. 30

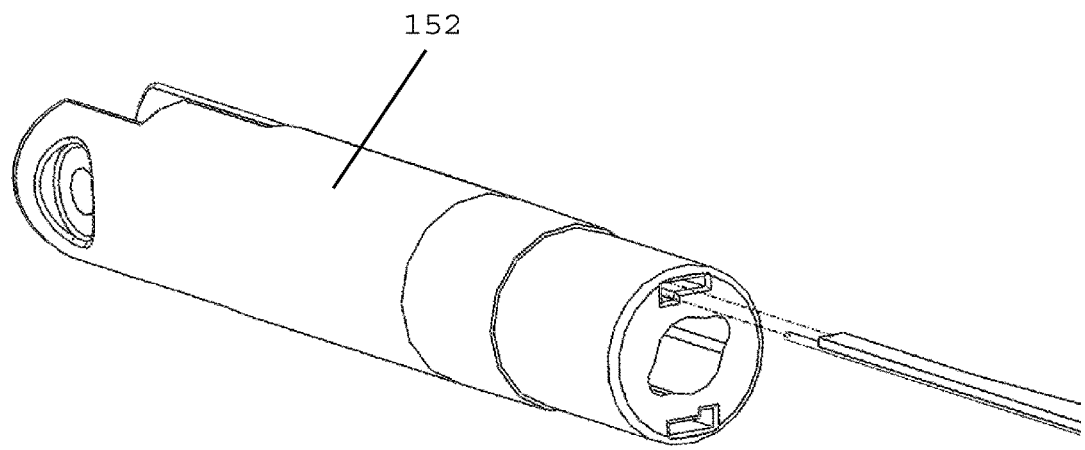
FIG. 31
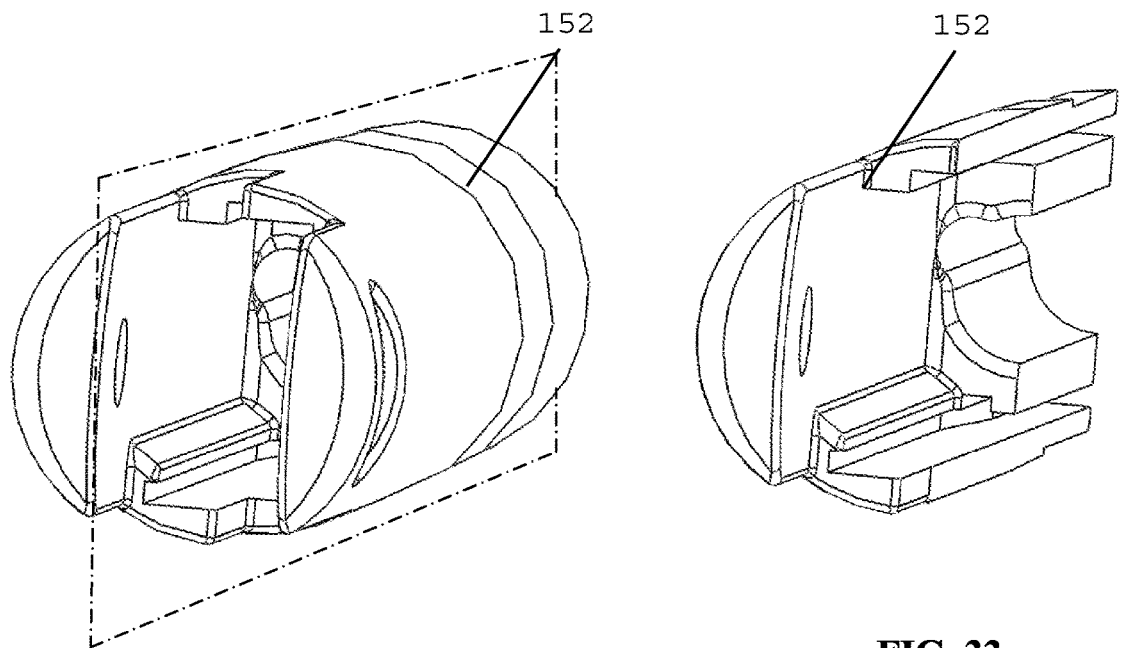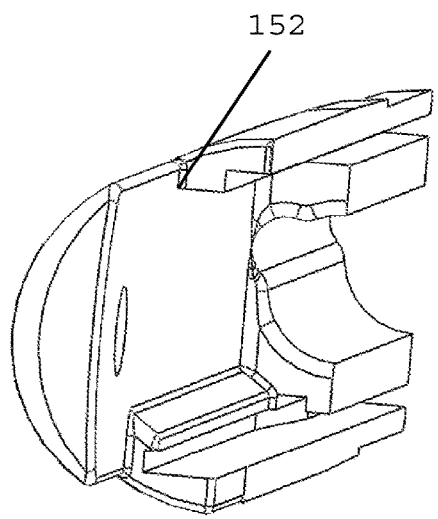
FIG. 32　　　　　　　　　　FIG. 33

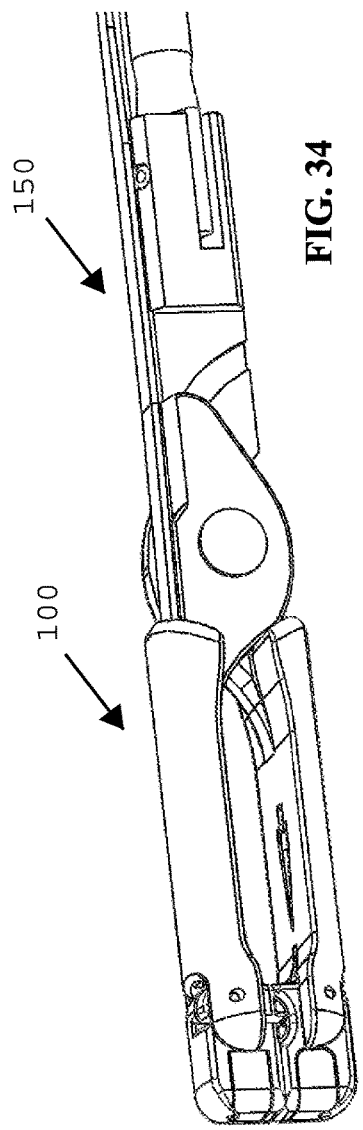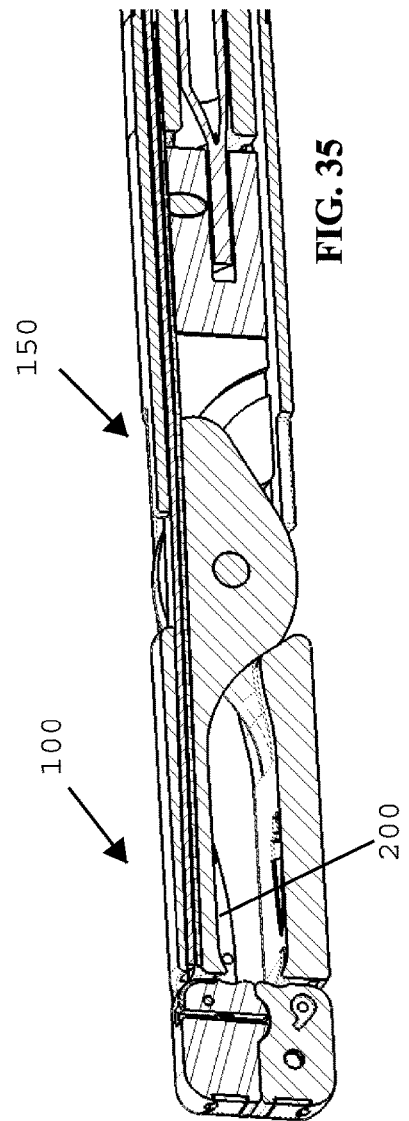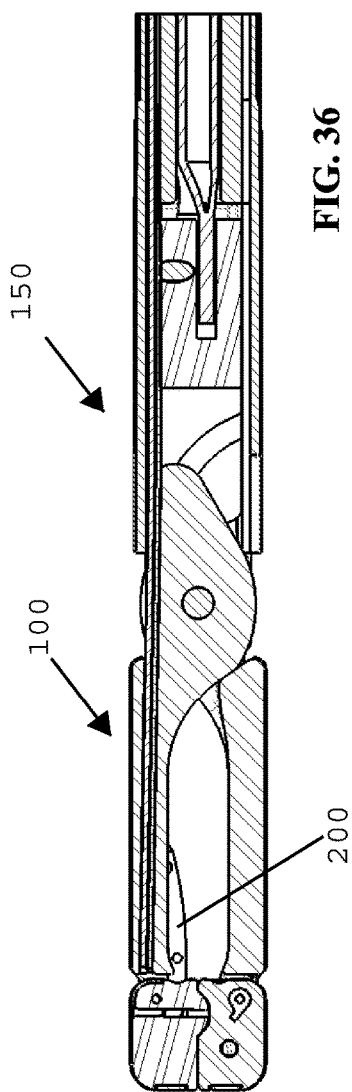

LAPAROSCOPIC SUTURING SYSTEM

CROSS REFERENCE TO RELATED APPLICATIONS

This application is a continuation of U.S. patent application Ser. No. 16/565,065, entitled, "LAPAROSCOPIC SUTURING SYSTEM," filed Sep. 9, 2019, which is a division of U.S. patent application Ser. No. 15/261,422, entitled, "LAPAROSCOPIC SUTURING SYSTEM," filed Sep. 9, 2016, which issued as U.S. Pat. No. 10,405,851, and which claims the benefit of U.S. Provisional Patent Application Ser. No. 62/217,502, entitled, "LAPAROSCOPIC SUTURING SYSTEM," filed Sep. 11, 2015. The above-referenced applications are incorporated by reference herein in their entireties.

BACKGROUND OF THE INVENTION

Field of the Invention

The present application relates to surgical instruments and more particularly to laparoscopic surgical devices for suturing tissue.

Description of the Related Art

In surgical procedures, such as minimally invasive surgical procedures in which a surgical site is accessed through a port, it can be desirable to suture tissue with a suturing tool that can be advanced through a relatively low-diameter port to the surgical site. A suturing tool can be configured to advance a needle and attached suture through tissue in the surgical site such that an operator can create a running stitch to approximate tissue. Suturing devices have been made that pass a needle down the trocar with the needle's longitudinal axis perpendicular to the trocar's axis, which limits the length of the needle that may be used in the device to the inner diameter of the trocar. Moreover, current suturing devices typically include operation mechanisms that are complex and cumbersome to operate, requiring multiple operational steps to complete a single stitch. Desirably, an improved suturing device can include increased efficiency, simplicity and ease of use.

SUMMARY OF THE INVENTION

In certain embodiments, a laparoscopic suturing device is provided herein. The laparoscopic suturing device comprises a handle assembly, an elongate shaft, a jaw assembly, and a needle. The handle assembly has a proximal end and a distal end. The elongate shaft extends distally from the distal end of the handle assembly and defines a central longitudinal axis. The jaw assembly extends distally from the elongate shaft. The jaw assembly comprises a first jaw and a second jaw each having a proximal end pivotably coupled to the elongate shaft and a distal end. The jaw assembly and the needle are selectively positionable between a stowed configuration in which the needle is positioned in one of the first jaw and the second jaw and the first jaw, the second jaw, and the needle are generally aligned with the central longitudinal axis and an open configuration in which the first jaw, the second jaw, and the needle extend transversely to the central longitudinal axis.

In certain embodiments, a laparoscopic suturing device is provided herein. The laparoscopic suturing device comprises a handle assembly, an elongate shaft, a jaw assembly, and a needle. The handle assembly has a proximal end and a distal end. The handle assembly comprises a trigger mechanism, a closure mechanism, and a toggle mechanism. The elongate shaft extends distally from the distal end of the handle assembly and defines a central longitudinal axis. The jaw assembly extends distally from the elongate shaft. The jaw assembly comprises a first jaw and a second jaw each having a proximal end pivotably coupled to the elongate shaft and a distal end. The trigger mechanism is operably coupled to the closure mechanism and the toggle mechanism such that an actuation cycle of the trigger mechanism sequentially actuates the closure mechanism to close the first jaw and the second jaw of the jaw assembly, actuates the toggle mechanism to transfer the needle from one of the first jaw and the second jaw to the other of the first jaw and the second jaw, and actuates the closure mechanism to open the first jaw and the second jaw.

In certain embodiments, a laparoscopic suturing system is provided herein. The laparoscopic suturing system comprises a laparoscopic suturing device and a suturing needle. The laparoscopic suturing device comprises a handle assembly, an elongate shaft, and a jaw assembly. The elongate shaft has a proximal end coupled to the handle assembly and a distal end. The elongate shaft defines a central longitudinal axis extending between the proximal end and the distal end. The jaw assembly is coupled to the distal end of the elongate shaft. The jaw assembly comprises a first jaw and a second jaw each pivotably coupled to the elongate shaft and pivotable between an open configuration and a closed configuration. The suturing needle is positionable in the jaw assembly. The suturing needle comprises a needle and a suture coupled to the needle. The needle has a generally curved profile and extends from a first penetrating tip to a second penetrating tip. The needle comprises a first shim notch adjacent the first penetrating tip, a second shim notch adjacent the second penetrating tip, a first recess adjacent the first penetrating tip, and a second recess adjacent the second penetrating tip.

In certain embodiments, a laparoscopic suturing device is provided herein. The laparoscopic suturing device comprises: a handle assembly, an elongate shaft, and a jaw assembly. The handle assembly has a proximal end and a distal end. The elongate shaft extends distally from the distal end of the handle assembly and defines a central longitudinal axis. The jaw assembly extends distally from the elongate shaft. The jaw assembly has a proximal end pivotably coupled to the elongate shaft and a distal end. The jaw assembly comprises a first jaw and a second jaw. The first jaw comprises a first base jaw at the proximal end of the jaw assembly; and a first flip jaw at the distal end of the jaw assembly. The first flip jaw is pivotably coupled to the first base jaw. The first flip jaw has a first needle channel. The first flip jaw is pivotable between a stowed position in which the first needle channel is oriented generally longitudinally with respect to the first base jaw and a suturing position in which the first needle channel is oriented transversely to the first base jaw. The second jaw comprises a second base jaw at the proximal end of the jaw assembly and a second flip jaw at the distal end of the jaw assembly. The second base jaw is pivotably coupled to the first base jaw and the elongate shaft. The second flip jaw is pivotably coupled to the second base jaw. The second flip jaw has a second needle channel. The second flip jaw is pivotable between a stowed position in which the second needle channel is oriented generally longitudinally with respect to the second base jaw and a suturing position in which the second needle channel is oriented transversely to the second base jaw.

In certain embodiments, a laparoscopic suturing device is provided herein. The laparoscopic suturing device comprises a handle assembly, an elongate shaft, and a jaw assembly. The handle assembly has a proximal end and a distal end. The handle assembly comprises a handle body, a trigger, and a toggle mechanism. The trigger is pivotally coupled to the handle body. The toggle mechanism is actuatable by pivotal movement of the trigger with respect to the handle body. The toggle mechanism comprises a toggle tube, a first shim, and a second shim. The toggle tube is rotatable within the handle body responsive to pivotal movement of the trigger. The toggle tube comprises a shim guide. The first shim has a proximal end with a first follower positioned in the shim guide. The first shim is longitudinally movable by rotation of the toggle tube. The second shim has a proximal end with a second follower positioned in the shim guide. The second shim is longitudinally movable by rotation of the toggle tube. The elongate shaft extends distally from the distal end of the handle assembly and defines a central longitudinal axis. The jaw assembly extends distally from the elongate shaft. The jaw assembly has a proximal end pivotably coupled to the elongate shaft and a distal end. The jaw assembly comprises a first jaw and a second jaw. The first jaw has a proximal end pivotably coupled to the elongate shaft and a distal end having a first needle retention slot therein. The second jaw has a proximal end pivotably coupled to the elongate shaft and a distal end having a second needle retention slot therein. The first shim extends distally to a distal end positioned in the first jaw and the second shim extends distally to a distal end positioned in the second jaw. The toggle mechanism is operable in a toggle cycle to alternately longitudinally advance the distal end of the first shim adjacent the first needle retention slot and advance the distal end of the second shim adjacent the second needle slot.

In certain embodiments, a laparoscopic suturing device is provided herein. The laparoscopic suturing device comprises a handle assembly, an elongate shaft, and a jaw assembly. The handle assembly has a proximal end and a distal end. The handle assembly comprises a latch mechanism having a latched configuration and an unlatched configuration. The elongate shaft extends distally from the distal end of the handle assembly and defines a central longitudinal axis. The jaw assembly extends distally from the elongate shaft. The jaw assembly has a proximal end pivotably coupled to the elongate shaft and a distal end. The jaw assembly comprises a first jaw and a second jaw. The first jaw comprises a first base jaw and a first flip jaw. The first base jaw is at the proximal end of the jaw assembly. The first flip jaw is at the distal end of the jaw assembly and pivotably coupled to the first base jaw. The first flip jaw is pivotable between a stowed position defining a low diametric profile of the jaw assembly and a suturing position. The second jaw comprises a second base jaw and a second flip jaw. The second base jaw is at the proximal end of the jaw assembly pivotably coupled to the first base jaw and the elongate shaft. The second flip jaw is at the distal end of the jaw assembly and pivotably coupled to the second base jaw. The second flip jaw is pivotable between a stowed position defining a low diametric profile to the jaw assembly and a suturing position. The latch mechanism is operably coupled to the first flip jaw and the second flip jaw such that with the latch mechanism in the latched position, the first flip jaw and the second flip jaw are maintained in the stowed position and with the latch mechanism in the unlatched position, the first flip jaw and the second flip jaw are pivotable to the suturing position.

BRIEF DESCRIPTION OF THE DRAWINGS

FIG. 13 is a top plan view of the jaw of FIG. 7 with a section line thereon;

FIG. 14 is a cross sectional view about the section line of the jaw of FIG. 7 in a suturing configuration;

FIG. 15 is a cross sectional view about the section line of the jaw of FIG. 7 partially rotated to a stowed configuration;

FIG. 16 is a cross sectional view about the section line of the jaw of FIG. 7 partially rotated to a stowed configuration;

FIG. 17 is a cross sectional view about the section line of the jaw of FIG. 7 rotated to the stowed configuration;

FIG. 28 is an end view of an embodiment of suturing needle for use in a laparoscopic suturing device;

FIG. 29 is a side view of the suturing needle of FIG. 28;

FIG. 30 is an isometric view of a base jaw of the jaw of FIG. 7;

FIG. 31 is a perspective view of a clevis of the actuation assembly of FIG. 25;

FIG. 32 is a perspective view of the clevis of FIG. 31 with a section plane illustrated in broken lines;

FIG. 33 is a cross sectional view of the clevis of FIG. 31 about the section plane;

FIG. 34 is a perspective view of the jaw assembly and actuation assembly of FIG. 25 with the clevis removed;

FIG. 35 is a perspective cross sectional view of the jaw assembly and actuation assembly of FIG. 34;

FIG. 36 is a cross sectional side view of the jaw assembly and actuation assembly of FIG. 34;

DETAILED DESCRIPTION OF THE INVENTION

In various embodiments, a suturing system is disclosed herein that can increase a surgeon's efficiency at applying sutures to tissue inside a patient during minimally invasive surgeries such as laparoscopic surgeries. The suturing device passes a needle with an attached suture back and forth through tissue between alternate jaws of a jaw assembly by driving the needle through tissue and using a receiving jaw to grip the needle while a driving jaw releases the needle.

During clinical use, an access device such as a trocar is first placed through a body wall and into a body cavity, leaving the trocar cannula disposed within the body cavity and across the body wall. The suturing devices discussed herein can utilize a suture that is attached to the center of a needle with sharp points on both ends so it may be passed back and forth through tissue. In order to fit the device down a relatively low diameter trocar such as a 5 mm trocar, the needle can be stowed away during insertion and removal through the trocar in order to lower the diametric profile of the device. When the needle is stowed away the device is considered to be in the deactivated or stowed state. When inside the body cavity or during needle loading outside the body, the device can be deployed into its activated or suturing state. While in its activated state, the device is able to drive a suturing needle through tissue and pass the needle and attached suture from a driving jaw to the receiving jaw.

Advantageously, the stowed needle configuration of the devices herein can allow the use of a needle with a length that otherwise would not fit down a 5 mm trocar. Allowing the surgeon to use a smaller trocar has considerable advantages, such as reducing post-operative healing time and scarring of the patient. Larger common size of trocars such as 10 mm, 12 mm and 15 mm would require a significantly larger incision than a 5 mm trocar. The stowed configuration of the devices herein obviates needle-length limitations of conventional suturing devices. The devices described herein can therefore stitch using a longer needle than the conventional 10 mm trocar diameter suturing devices while being able to traverse through a 5 mm trocar. This use of a longer needle can advantageously allow more tissue or thicker tissue to be penetrated, allowing the surgeon to suture more than 10 mm devices allow.

Figure 1:
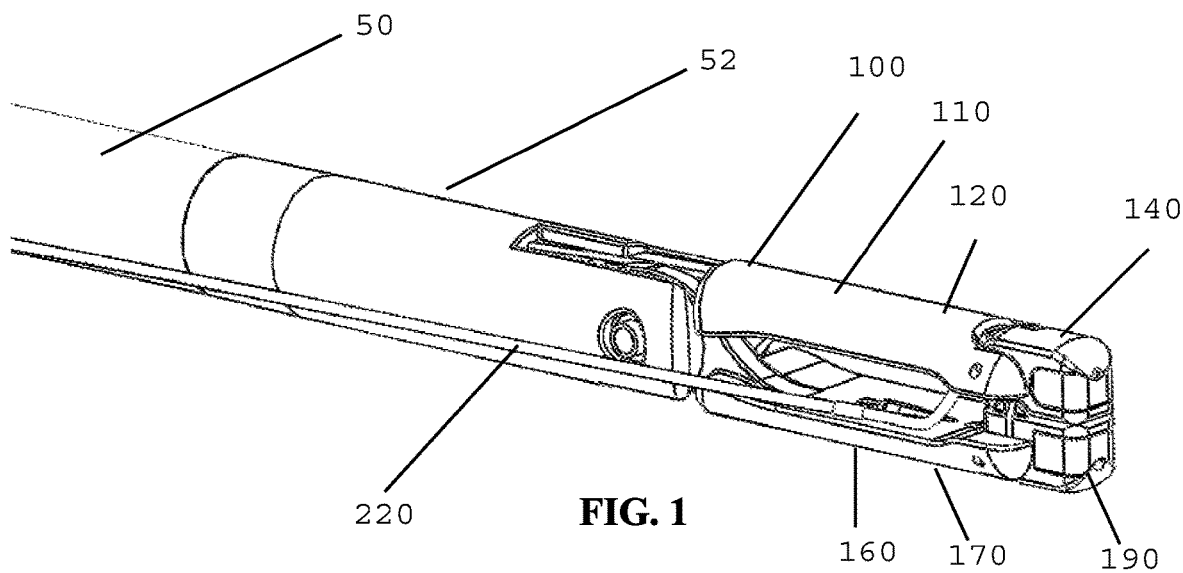
FIG. 1 is an isometric view of an embodiment of jaw assembly for a laparoscopic suturing device in a stowed configuration.
Figure 2:
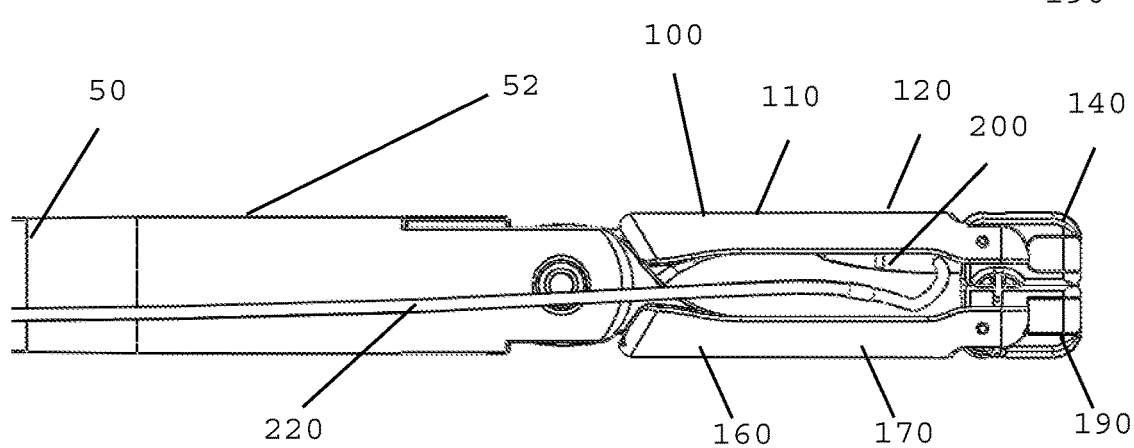
FIG. 2 is a side view of the jaw assembly of FIG. 1.
Figure 3:
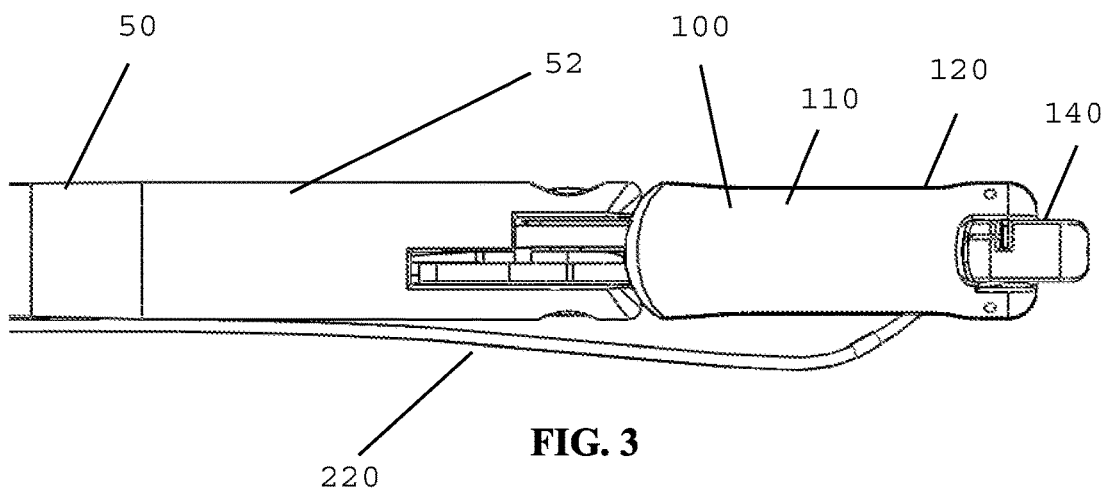
FIG. 3 is a top plan view of the jaw assembly of FIG. 1.

With reference to FIGS. 1-6, various aspects of an embodiment of a distal end of a laparoscopic suturing device 10 including an elongate shaft 50 and a jaw assembly 100 are illustrated. FIGS. 1-3 illustrate isometric, side, and top views of the jaw assembly 100 in a stowed configuration retaining a needle 200 and suture 220. In the stowed configuration, the jaw assembly 100 has a relatively small outer diameter for insertion through a laparoscopic surgical port such as a trocar cannula. As illustrated, with the jaw assembly in the stowed configuration, the needle 200 is retained by one of the jaws 110, 160 and the suture 220 extends proximally from the needle along the elongate shaft 50.

In certain embodiments, the jaw assembly 100 can be sized for insertion through one of a number of trocar cannula sizes, such as a trocar cannula for receiving 5 mm instruments, 10 mm instruments, 12 mm instruments, or 15 mm instruments. Advantageously, the suturing device herein having a low profile stowed jaw assembly configuration can allow a relatively large needle to be deployed through an instrument sized for a relatively small trocar.

With continued reference to FIGS. 1-3, in the illustrated embodiment, the jaw assembly 100 comprises a first jaw 110 and a second jaw 160 each having a proximal end pivotably coupled to one another and to a distal end 52 of the elongate shaft 50. The first jaw 110 can comprise a first base jaw 120 having a proximal end pivotably coupled to the elongate shaft 50 and a distal end. The first jaw 110 can further comprise a first flip jaw 140 pivotably coupled to the distal end of the first base jaw 120. In the illustrated embodiment, similarly, the second jaw 160 can comprise a second base jaw 170 having a proximal end pivotably coupled to the elongate shaft 50 and a distal end with a second flip jaw 190 pivotably coupled thereto.

Figure 4:
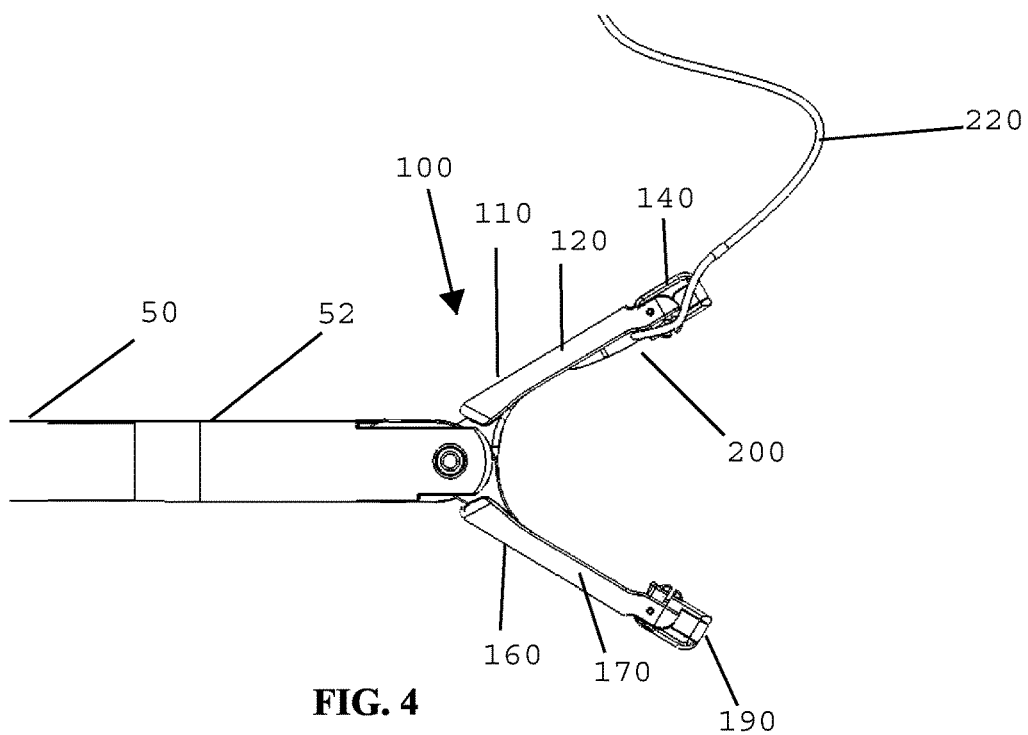
FIG. 4 is a side view of the jaw assembly of FIG. 1 with the base jaws in an open state and flip jaws in the stowed configuration.
Figure 5:
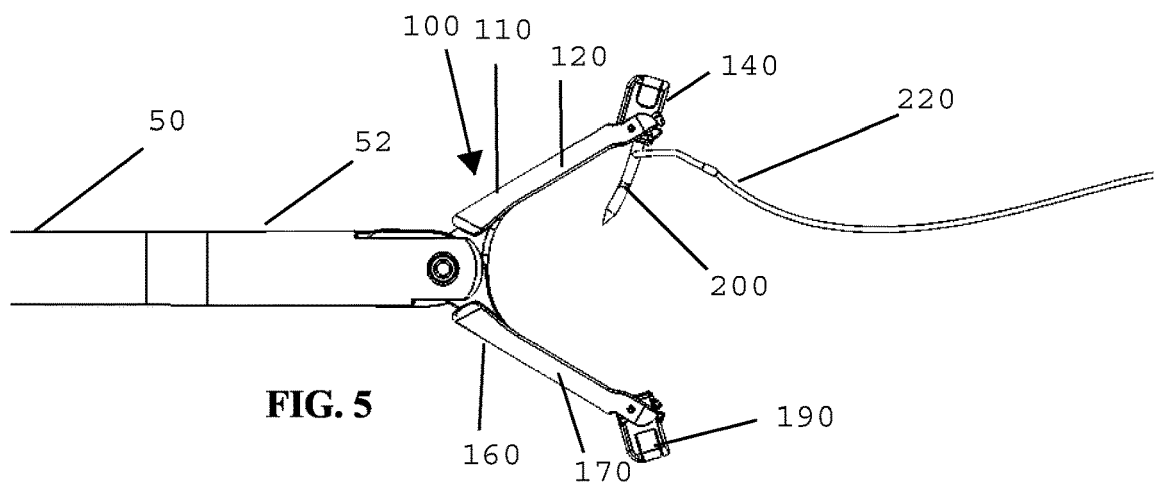
FIG. 5 is a side view of the jaw assembly of FIG. 1 with the base jaws in an open state and flip jaws partially rotated to a suturing configuration.
Figure 6:
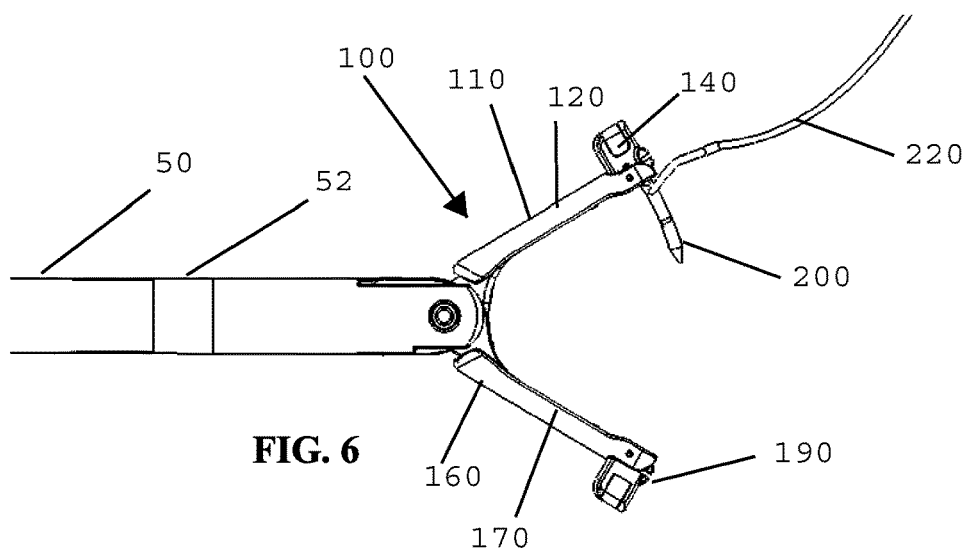
FIG. 6 is a side view of the jaw assembly of FIG. 1 with the base jaws in an open state and flip jaws rotated to a suturing configuration.

With reference to FIGS. 4-6, further aspects of an embodiment of jaw assembly 100 of the laparoscopic suturing device 10 are illustrated. In FIGS. 4-6, side views of a sequence of operation of the jaw assembly from the stowed configuration to a suturing configuration are illustrated. FIG. 4 illustrates the jaw assembly 100 with the jaws 110, 160 having their base jaws 120, 170 in an open position pivoted such that their distal ends are spaced apart from one another and their flip jaws 140, 190 pivoted to a stowed configuration. As further discussed herein with reference to FIGS. 61-63, a latch mechanism can be actuated by a user to pivot the flip jaws 140, 190 from the stowed configuration (FIG. 4) through a partially-rotated position (FIG. 5) to a suturing configuration (FIG. 6).

Figure 7:
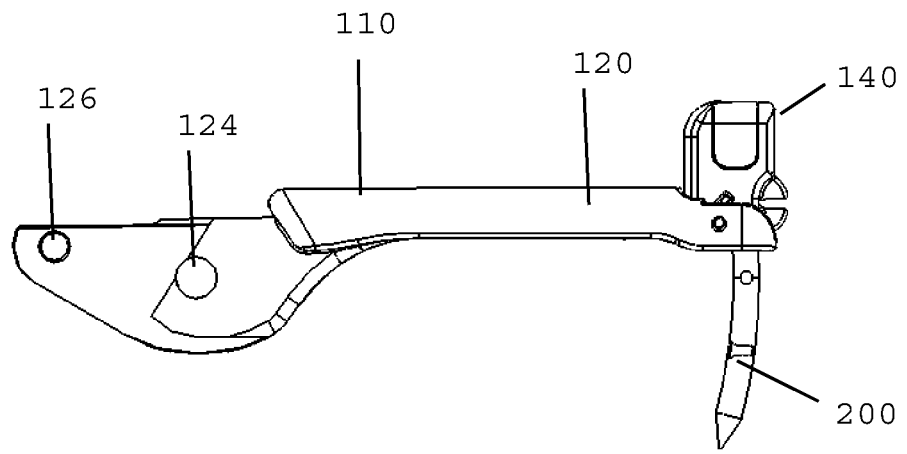
FIG. 7 is a side view of one jaw of the jaw assembly of FIG. 1 with a suturing needle disposed therein.
Figure 8:
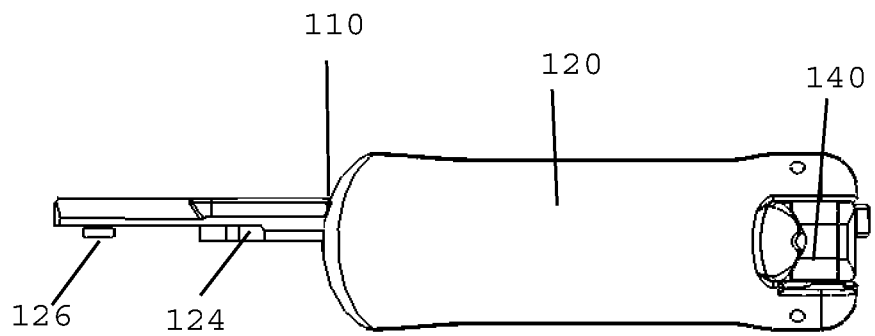
FIG. 8 is a top view of the jaw of FIG. 7.
Figure 9:
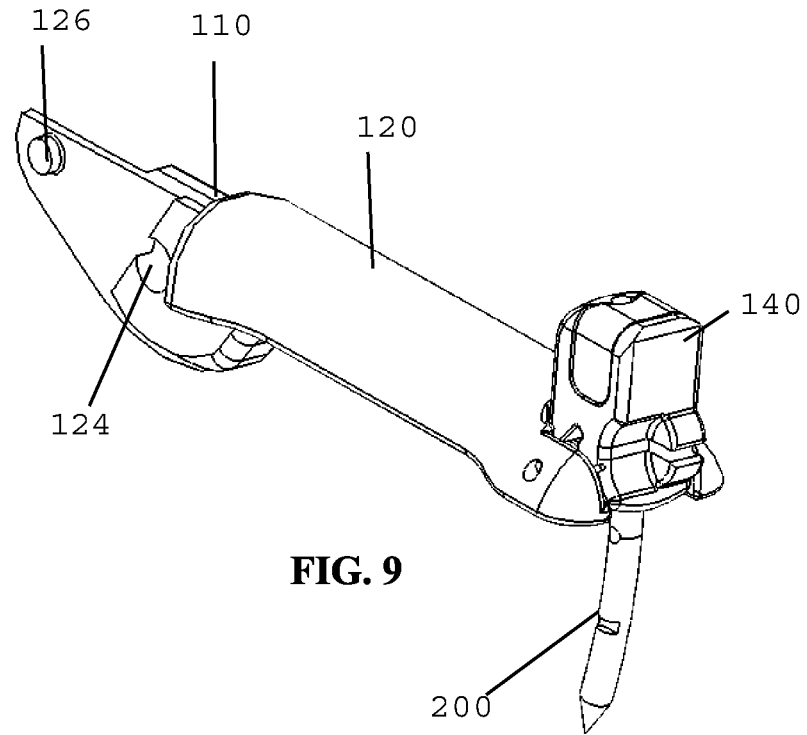
FIG. 9 is an isometric view of the jaw of FIG. 7 with the suturing needle disposed therein.

With reference to FIGS. 7-12, various aspects of a first jaw 110 of an embodiment of jaw assembly 100 and a needle 200 are illustrated. FIGS. 7-9 illustrate side, top and isometric views of the first jaw 110 with the first flip jaw 140 in the suturing configuration with the needle 200 positioned therein. A proximal end of the first base jaw 120 can comprise a pivot 124 such as an aperture therethrough to receive a rivet or pinned connection with the second jaw 160 and the distal end 52 of the elongate shaft 50. The proximal end of the first base jaw 120 can further comprise an actuation post 126 such that the first base jaw 120 can be pivoted about the pivot 124 by actuation of the post 126 by a jaw actuation mechanism. The first base jaw has a jaw body extending distally from the pivot 124 to a distal end. The first flip jaw 140 is pivotably coupled to the distal end of the first base jaw 120.

Figure 10:
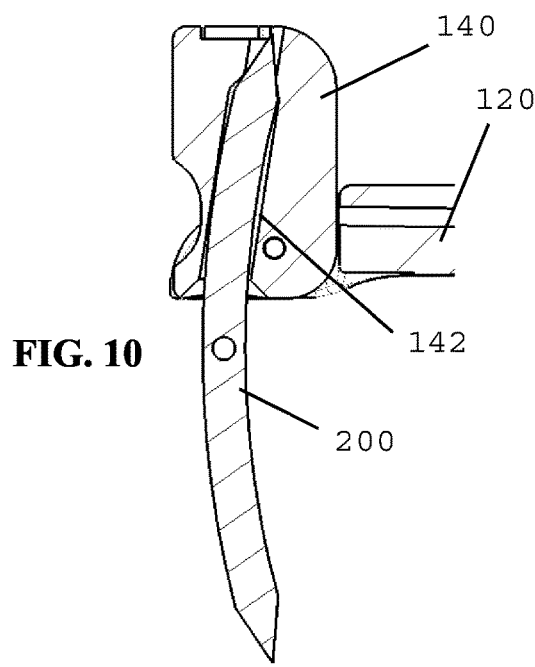
FIG. 10 is a cross-sectional view of a flip jaw and suturing needle of the jaw of FIG. 7.
Figure 11:
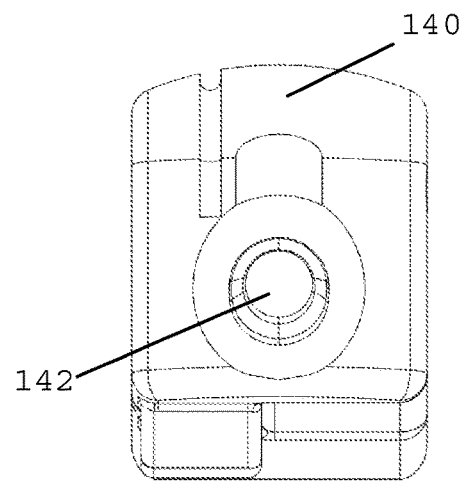
FIG. 11 is a lower plan view of a flip jaw for the jaw of FIG. 7

With reference to FIG. 10, a cross sectional view of the distal end of the first jaw 110 is illustrated. The first flip jaw 140 can have a needle receiving channel 142 formed therein. With the first flip jaw 140 pivoted to the suturing position, the needle receiving channel 142 is positioned generally transverse to a longitudinal axis of the first base jaw 120 to align with a curvature of the needle. Additionally, with reference to FIG. 11, the needle receiving channel 142 can have an oblong or eccentric cross sectional profile to maintain a rotational orientation of the needle 200 with respect to the needle receiving channel 142.

With continued reference to FIG. 10, in some embodiments, to increase manufacturability, the flip jaw's needle receiving channel can be a straight hole to allow the use of a non-rotating core pin during injection molding. The straight hole can be angled to be tangent to a circle drawn about the base jaw pivot centerline. The core pin can be inserted at an angle to account for a curvature of the needle. The core pin hole can be elliptical or an elongated oval to minimize the ability of the curved needle to rotate while seated in the hole. The major axis of the elliptical cross section can be oriented in the direction of the needle bend to account for the curvature of the needle. In a section view going through the needle hole of the flip jaw in the direction of the needle curvature, the needle can have three contact points to prevent motion. The width of the minor axis of the cross sectional ellipse would be the needle diameter plus clearance to prevent the needle from twisting around its longitudinal axis while seated in the hole.

Figure 12:
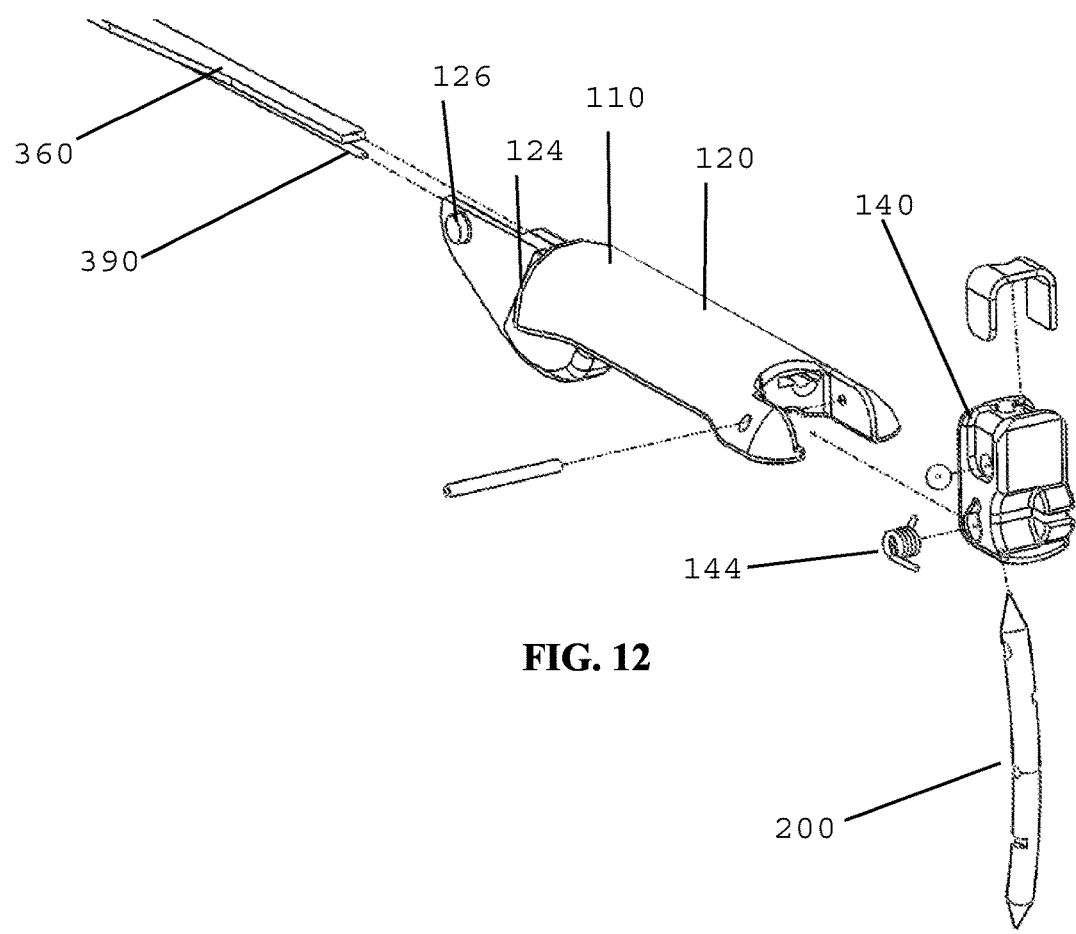
FIG. 12 is an exploded view of the jaw of FIG. 7.

With reference to FIG. 12, an exploded view of an embodiment of the first jaw 110 is illustrated. In the illustrated embodiment, the first flip jaw 140 is pivotably coupled to the first base jaw 120 with a pinned connection. In some embodiments, the first flip jaw 140 can be biased to the suturing position by a biasing member such as a torsion spring 144 positioned about a rotational axis of the flip jaw 140 between the flip jaw 140 and the base jaw 120. A first cable 390 and a first shim 360 can extend through a slot in the first base jaw 120 to the first flip jaw 140 to be selectively actuated by a user in an operation sequence through operation of a latching mechanism and toggle mechanism as further described below.

With reference to FIGS. 14-17, cross sectional views of an embodiment of first jaw 110 about a section line illustrated in FIG. 13 are illustrated. FIGS. 14-17 illustrate an operating sequence of the first flip jaw 140 during operation of the latching mechanism such that the first flip jaw is pivoted from the suturing configuration (FIG. 14) through partially-stowed configurations (FIGS. 15-16) to the stowed configuration (FIG. 17). Operation of the latch mechanism can increase tension on the first cable 390 extending through a slot or channel formed longitudinally in the first base jaw 120 to pivot the first flip jaw 140 relative to the first base jaw. While the first torsion spring 144 (FIG. 12) can be used to bias the first flip jaw 140 to a suturing configuration once the suturing device has been introduced to a surgical field, it is contemplated that following use of the suturing device, a tensioned cable can advantageously provide reliable, robust rotation of the flip jaw 140 to the stowed position even where accumulation of fluid or tissue may otherwise resist or prevent rotation of the flip jaw. In other embodiments, the torsion spring 144 can be replaced with an additional cable such that the latching mechanism utilizes a first cable to pivot the flip jaw to a suturing configuration in an unlatching operation and the illustrated cable to pivot the flip jaw to the stowed configuration in the latching operation.

Figure 18:
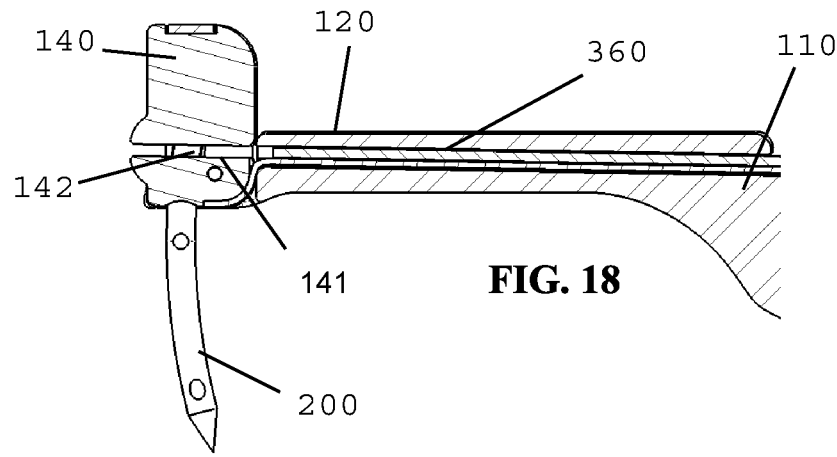
FIG. 18 is a cross sectional view about the section line of the jaw of FIG. 7 in a suturing configuration.
Figure 19:
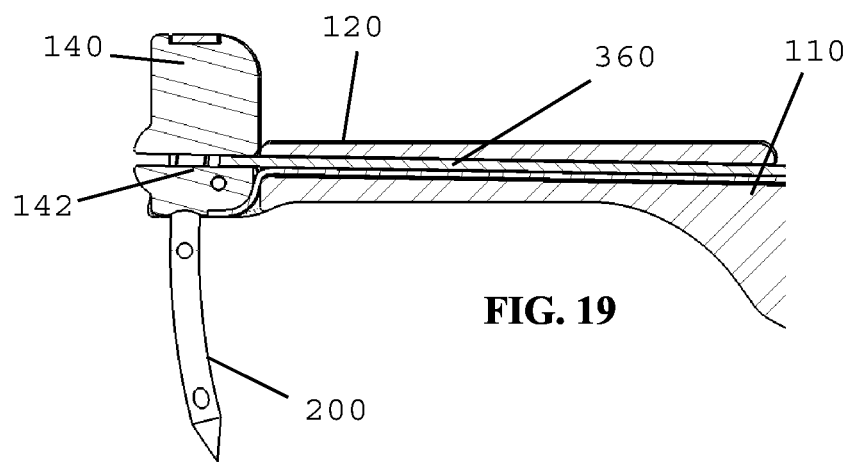
FIG. 19 is a cross sectional view about the section line of the jaw of FIG. 7 in a suturing configuration with a shim partially advanced to lock the flip jaw.
Figure 20:
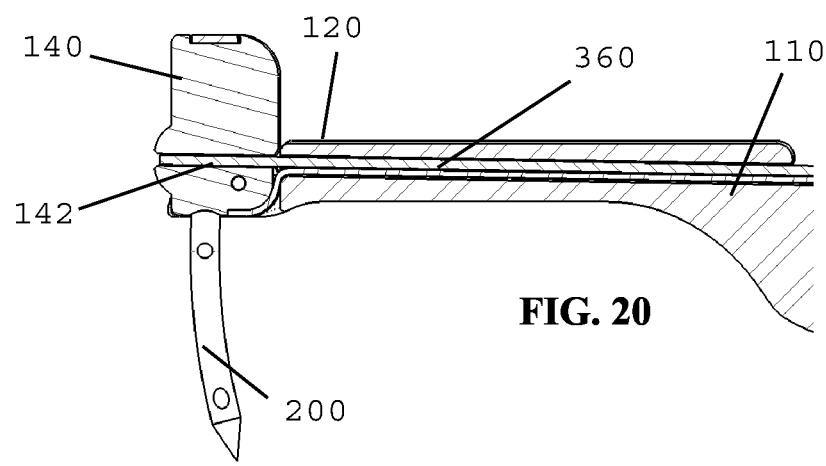
FIG. 20 is a cross sectional view about the section line of the jaw of FIG. 7 in a suturing configuration with a shim advanced to latch the flip jaw and retain the suturing needle.
Figure 21:
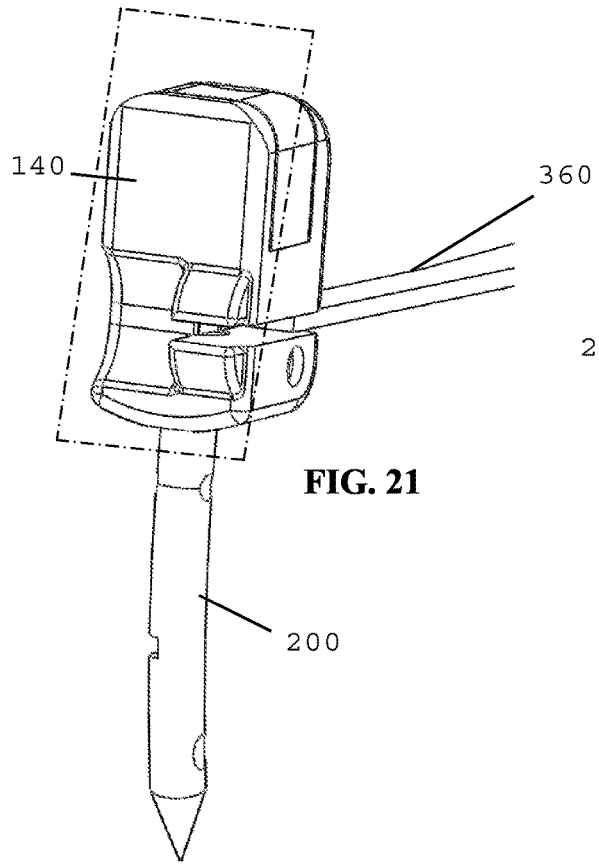
FIG. 21 is a perspective view of the flip jaw and needle of the jaw of FIG. 7 with a section plane illustrated in broken lines.

FIGS. 18-20 illustrate cross-sectional views of the first jaw 110 in an operating sequence of the toggle mechanism to advance a distal end of the first shim 360 distally through a slot or shim channel 141 in the first flip jaw 140. Distal advancement of the first shim 360 through the shim channel 141 extending through the first flip jaw 140 (FIG. 19) locks the first flip jaw 140 in the suturing configuration. The shim channel 141 can traverse the needle receiving channel. With the needle 200 positioned in the needle receiving channel 142, a shim notch 210 of the needle is generally aligned with the shim channel 141 of the first flip jaw 140. Accordingly, further advancement of the first shim 360 extends the shim distally to engage an interference feature such as a first slot or shim notch 210 (FIGS. 28-29) in the needle 200 to latch the needle 200 into the first flip jaw (FIG. 20). The shim channel 141 in the first flip jaw 140 can extend distally beyond the needle receiving channel 142 such that the first shim can engage the first flip jaw 140 proximal and distal of the needle receiving channel 142 and be recessed from tissue. In some embodiments, a distal surface of the first flip jaw 140 can include a protrusion formed thereon having the slot therein to allow additional distal movement of the first shim 360. While the illustrated embodiment includes a single shim to lock both the flip jaw and needle, in other embodiments, it is contemplated that locking of the needle and flip jaw can be accomplished using two separate mechanisms. In these embodiments, a shim can be used to lock the needle, and the flip jaw may be locked by another mechanism such as a second shim, sliding bolt, or pin.

Figure 22:
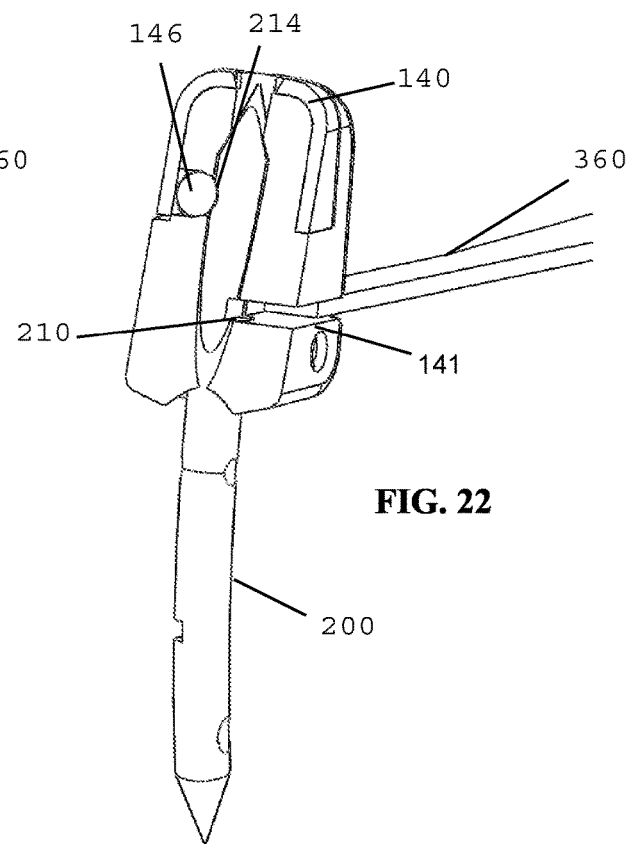
FIG. 22 is a cross sectional view of the flip jaw and needle of FIG. 21 about the section plane.

With reference to FIGS. 21-24, various views of the first flip jaw 140, needle 200 and first shim 360 (FIGS. 21-22) are illustrated. FIG. 22 illustrates a sectional view of the first flip jaw about the sectional plane indicated in broken lines in FIG. 21 with the shim 360 partially advanced into the shim channel 141 in the first flip jaw 140. The first flip jaw can include a retention feature such as a generally spherical detent 146 positioned therein to engage a corresponding mating recess 214 in the needle 200. This detent engagement can advantageously maintain the position of the needle 200 within the flip jaw when the first flip jaw 140 is in the stowed configuration and before the toggle mechanism has completely advanced the first shim 360 to engage the first shim notch 210 of the needle. In some embodiments, the detent can have a leaf spring wrapped around the flip jaw that applies force to a ball. The ball can reside inside a cylindrical channel that intersects with the needle hole in the flip jaw. The channel narrows near the needle hole to prevent the ball from falling out when no needle is present. When a needle is in the flip jaw, the ball is pressed into a corresponding recess in the needle to retain it while the shims are not locking the needle in place. In other embodiments, instead of the ball of the illustrated embodiment, the needle detent of the flip jaw can be an elastomeric protrusion, a shaped leaf spring tab, or a magnet.

Figure 23:
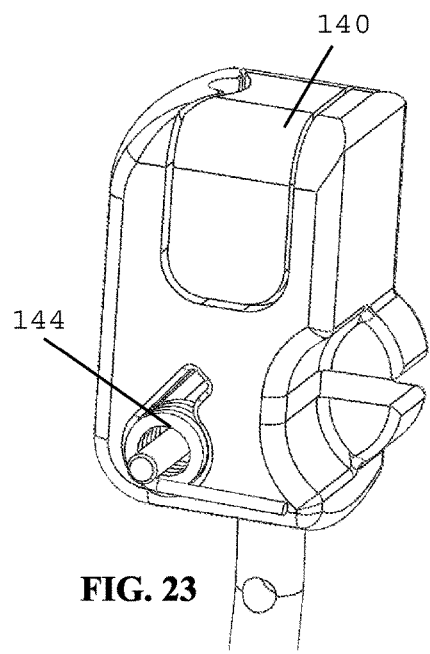
FIG. 23 is a side view of the flip jaw and needle of FIG. 21.

FIG. 23 illustrates the first torsion spring 144 positioned about the pivot axis of the first flip jaw 140. The illustrated embodiment of first flip jaw 140 also includes the distal protrusion beyond the needle retention channel. As illustrated, one portion of the distal surface of the first flip jaw 140 protrudes from an otherwise generally planar face and includes the shim slot therethrough. An adjacent portion of the distal surface of the first flip jaw is recessed such that the first flip jaw 140 can be nested with the second flip jaw in a low profile configuration having a relatively small outer diameter with the jaw assembly in the stowed configuration.

Figure 24:
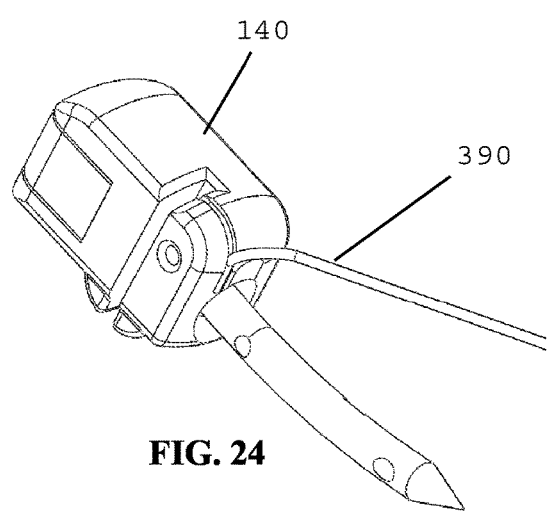
FIG. 24 is a perspective view of the flip jaw and needle of FIG. 21 with an actuation cable attached thereto.

FIG. 24 illustrates the first cable 390 of the latch mechanism coupled to the first flip jaw. The first cable 390 is coupled to the first flip jaw at a location offset from the pivot axis such that tension in the cable tends to pivot the first flip jaw towards the stowed configuration. The first flip jaw 140 can include a cable slot in an outer surface thereof to receive the first cable 390 when the first flip jaw 140 has been pivoted to the suturing configuration.

Figure 25:
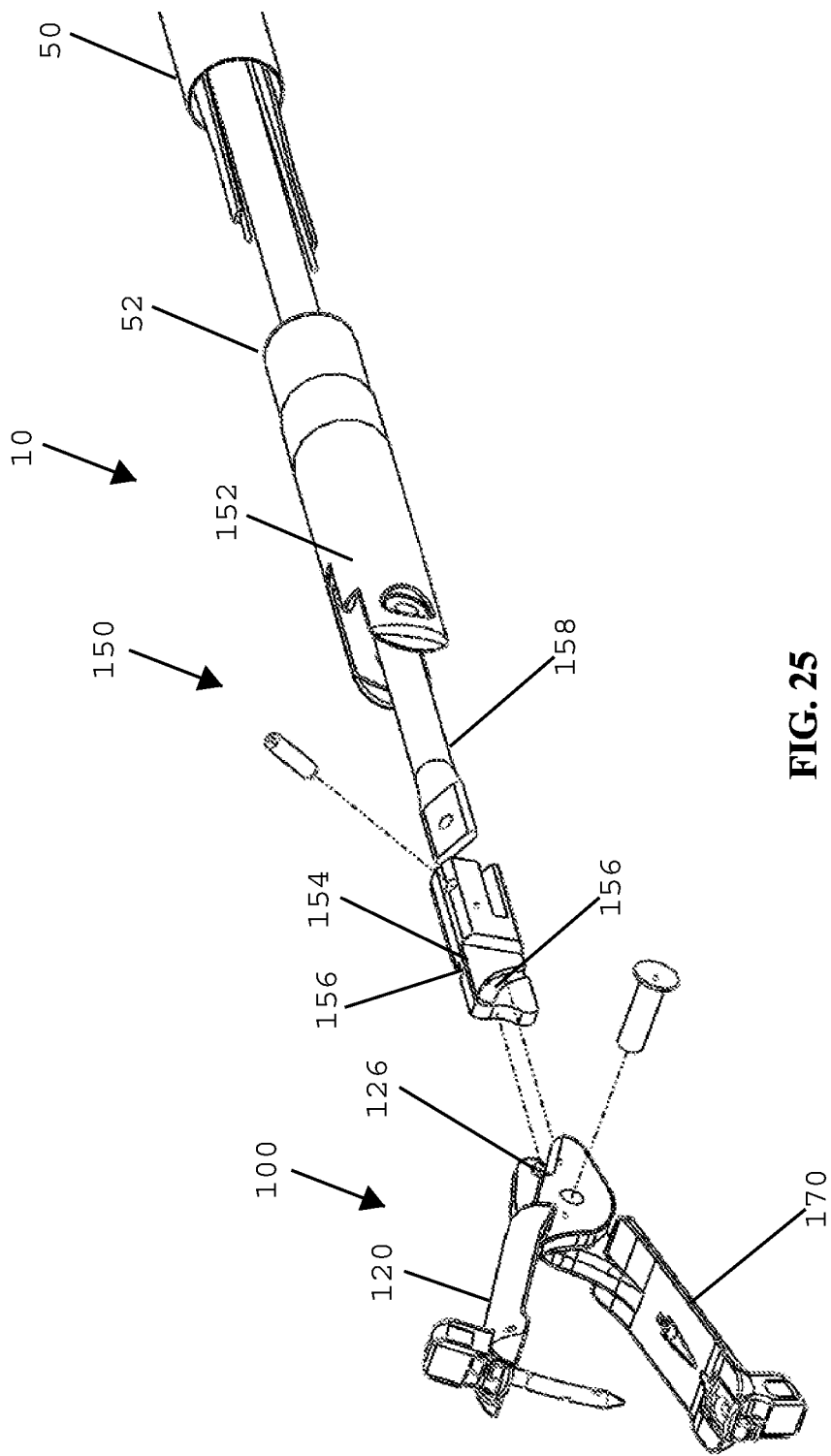
FIG. 25 is an exploded view of an embodiment of jaw assembly and an actuation assembly for a laparoscopic suturing device.

With reference to FIG. 25, an exploded view of a distal end of laparoscopic suturing device 10 is illustrated. As illustrated, the distal end includes the jaw assembly 100, a jaw actuation mechanism 150, and a distal end 52 of an elongate shaft 50. In the illustrated embodiment, the jaw assembly includes first and second jaws 110, 160 that are pivotably coupled to one another and are substantially similar. It is contemplated that in other embodiments of jaw assembly for use in the suturing device herein, a suturing device can include jaws having different configurations. For example, a jaw assembly can include a single pivotable jaw and a single stationary jaw or only one jaw having a pivotable flip jaw. Thus, in some embodiments, a jaw assembly can include a first jaw comprising a first base jaw and a first flip jaw pivotably coupled to the first base jaw in which the needle can be positioned in a stowed configuration, and a second jaw pivotably coupled to the distal end of the elongate shaft, but having a needle recess therein with no corresponding second flip jaw. In other embodiments, the second jaw can extend longitudinally distally from the elongate shaft and be pivotably fixed relative to the elongate shaft.

With continued reference to FIG. 25, the jaw actuation mechanism 150 can include a clevis 152 and an actuator 154. The clevis 152 can contain guiding slots for the shims and cables to prevent buckling. A slotted head of the actuator 154 can support the shims and cables from underneath to prevent buckling inside the clevis. The clevis can be formed at or positioned on the distal end 52 of the elongate shaft 50. The first and second jaws can be pivotably coupled to the clevis 152. The slotted head of the actuator 154 can include actuation slots 156 formed therein. In the illustrated embodiment, a drive rod 158 is slideable within the elongate shaft 50 and is coupled to the actuator 154 to advance the actuator 154 proximally and distally relative to the elongate shaft 50. Actuation posts 126 of the first and second base jaws 120, 170 can be positioned within the actuation slots 156 such that longitudinal translation of the actuator 154 opens and closes the base jaws 120, 170.

Figure 26:
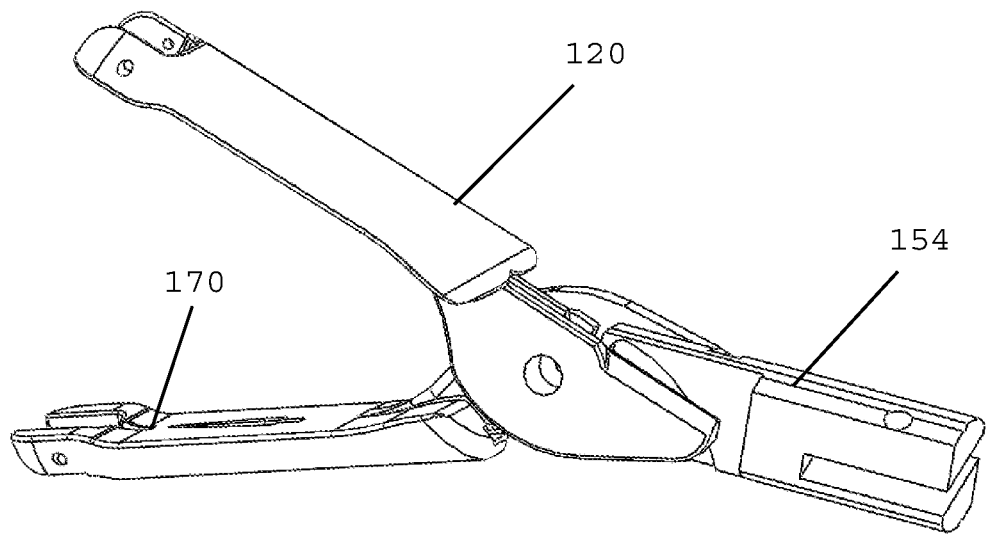
FIG. 26 is a perspective view of base jaws of the jaw assembly of FIG. 25 in an open configuration.
Figure 27:
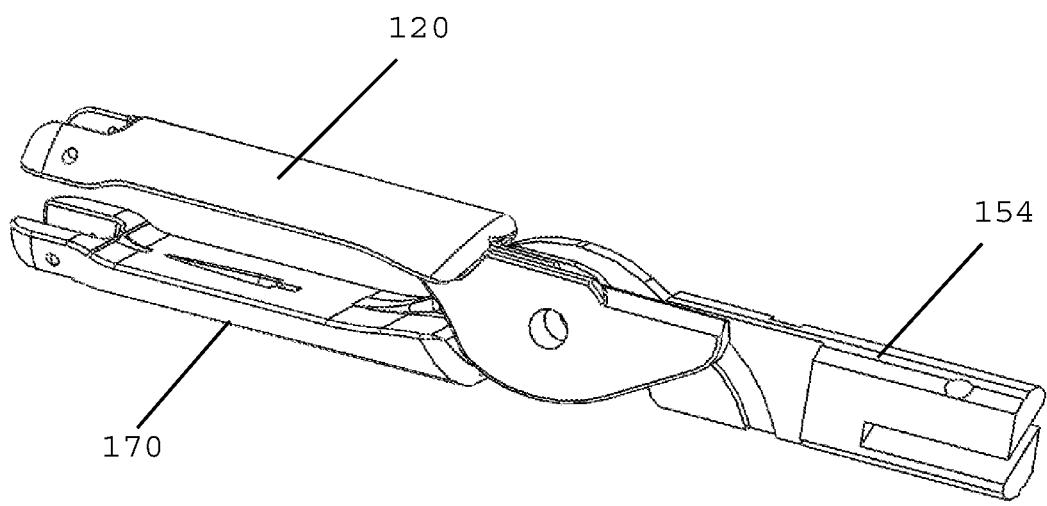
FIG. 27 is a perspective view of base jaws of the jaw assembly of FIG. 25 in a closed configuration.

FIGS. 26-27 illustrate the actuator 154, first base jaw 120, and second base jaw 170. As illustrated, the actuator 154 can be translated longitudinally to pivot the base jaws 120, 170 relative to one another such that the base jaws 120, 170 can be selectively positioned in an open (FIG. 26) or closed (FIG. 27) configuration.

With reference to FIGS. 28-29, an embodiment of suturing needle is illustrated. As illustrated, the needle 200 includes a first shim notch 210 adjacent a first penetrating tip, a second shim notch 212 adjacent a second penetrating tip, a first recess 214 adjacent the first penetrating tip, and a second recess 216 adjacent the second penetrating tip. By alternating which shim is locking the needle, the needle may be passed between the two jaws of the device. Advantageously, the needle also has detent features provided by the first and second recesses 214, 216 that allow the jaws to grip the needle while there are no shims locking the needle in place (i.e. in the stowed configuration). The needle can also include an aperture 218 for receiving a suture therethrough. It is contemplated that in some embodiments, the suture can include a leader segment such as a braided metallic or polymeric segment coupled to the needle 200 at the aperture 218 and a suturing segment coupled to the leader such as at a crimp joint. In various embodiments, the leader segment can be knotted, adhered with adhesive, heat forming, or tied about the needle. In various embodiments, the leader segment and suturing segment can be fixed by knotting the suture and leader, heat forming the suture and leader inside, or adhered with adhesive. The suturing segment can be a monofilament polymeric suture.

Desirably, this suture construction with a braided leader and monofilament suturing segment can be resilient and enhance usability. Driving the needle through tissue can cause repeated bending of the leader at the needle/leader interface. Having a more flexible material can reduce the likelihood of breakage due to repeated bending of the material at this interface. This flexibility also decreases the amount of force to drive the needle through tissue since the material bends easier and therefore reduces the profile. In some embodiments, the leader can be inserted into the needle aperture, and then crimped in the aperture. The leader can be connected to the suture by a stainless steel crimped tube. The suture may also be braided to increase flexibility. In some embodiments, the leader can be braided stainless steel to desirably provide enhanced strength and allow welding to the needle.

In some embodiments, the suturing segment can comprise a monofilament or braided suture that is unidirectionally barbed to prevent it from retracting through the tissue and causing wound dehiscence. This retention feature would eliminate the need for the surgeon to tie knots after every stitch, which improves the efficiency and ease of the surgery. An end of the suture opposite the needle can have an anchor to prevent further migration into the tissue and wound dehiscence. In some embodiments, the anchor can comprise a fixed or variable diameter loop that the suture is threaded through after the first pass through tissue, resulting in a knotless anchored end. The suturing is then continued without the need to tie any knots. In other embodiments, the anchor of the suture can comprise a T-shaped anchor. Desirably, a T-shaped anchor can eliminate the need for threading the suture through an anchor loop after the first pass through tissue.

With continued reference to FIG. 29, in the illustrated embodiment, the needle can comprise a double headed configuration with penetrating tips disposed at opposite ends thereof. A central body of the needle can be generally curved. In some embodiments, the needle is curved to have a bend radius that is equal to the distance from the needle to the base jaw's pivot centerline. This bend radius can help guide the needle through tissue and can minimize the amount of torque that could bend the needle during the piercing of tissue. In other embodiments, the needle can comprise a single headed configuration with a single penetrating tip disposed at one end thereof.

With reference to FIGS. 30-33, an embodiment of first base jaw 120 (FIG. 30) and an embodiment of clevis 152 are illustrated. As illustrated, both the base jaws 120, 170 and clevis 152 can include passages such as longitudinal slots or channels to facilitate operation of the shims and cables.

Figure 37:
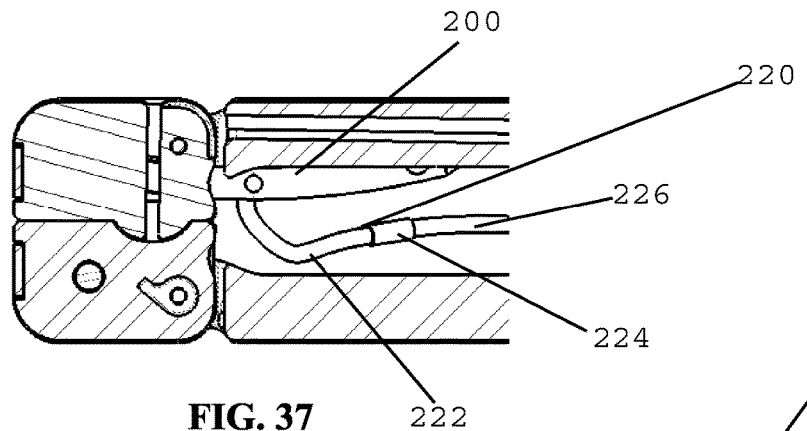
FIG. 37 is a cross sectional side view of the distal end of the jaw assembly of FIG. 1 in the stowed configuration.

With reference to FIGS. 34-37, the jaw assembly 100 and jaw actuation mechanism 150 are illustrated with the jaw assembly in a stowed configuration with a needle 200 in one of the jaws. FIG. 37 illustrates the needle 200 with a suture 220 having a leader 222, crimp 224, and suturing segment 226 attached thereto.

Figure 38:
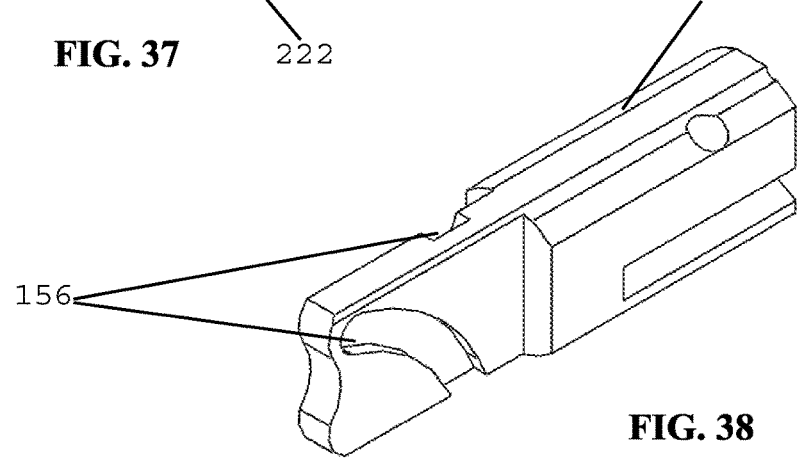
FIG. 38 is an isometric view of an embodiment of a slotted actuator of the actuation assembly of FIG. 25.
Figure 39:
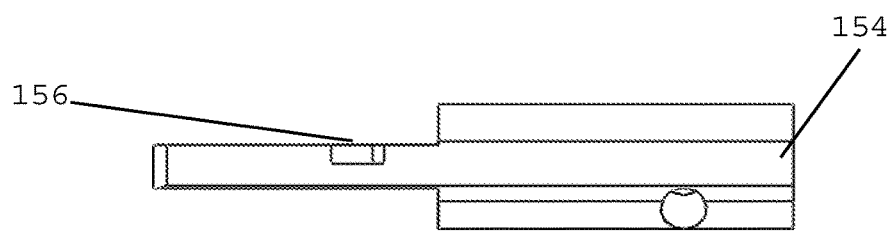
FIG. 39 is a top view of the slotted actuator of FIG. 38.
Figure 40:
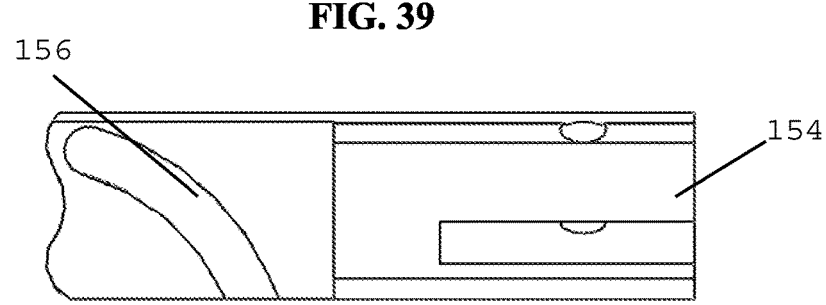
FIG. 40 is a side view of the slotted actuator of FIG. 38.

With reference to FIGS. 38-40, an embodiment of actuator 154 for the jaw actuation mechanism is illustrated. As illustrated, the actuator comprises a slotted actuation member having actuation slots 156 on opposing surfaces thereof. The slotted portion of the actuation member can be positioned between the first base jaw and the second base jaw proximal of the pivot such that actuation posts of the base jaws are each received in an actuation slot 156.

Figure 41:
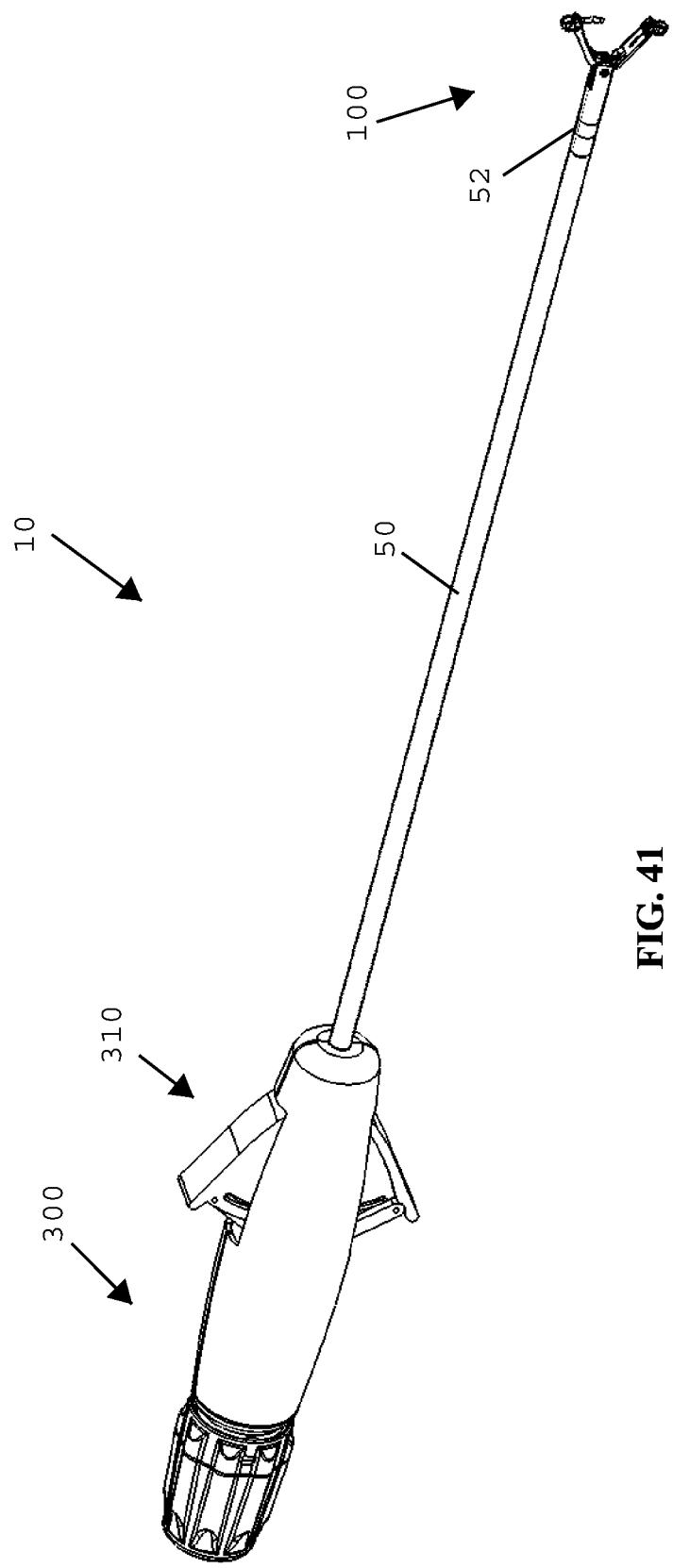
FIG. 41 is an isometric view of an embodiment of suturing device having the jaw assembly of FIG. 1.

With reference to FIG. 41, an embodiment of laparoscopic suturing device 10 is illustrated. The suturing device 10 can include a handle assembly 300, an elongate shaft 50, and a jaw assembly 100. The handle assembly can extend generally longitudinally from a proximal end to a distal end. The handle assembly 300 can include a trigger mechanism 310 including pivotable levers protruding from the handle assembly. In other embodiments, it is contemplated that other handle and trigger configurations can be used with various aspects of jaw assembly mechanism described herein. The elongate shaft 50 extends distally from the distal end of the handle assembly and defines a central longitudinal axis of the suturing device 10. The jaw assembly 100 can include a pair of opposing jaws pivotably coupled to one another and to the distal end 52 of the elongate shaft 50.

Figure 42:
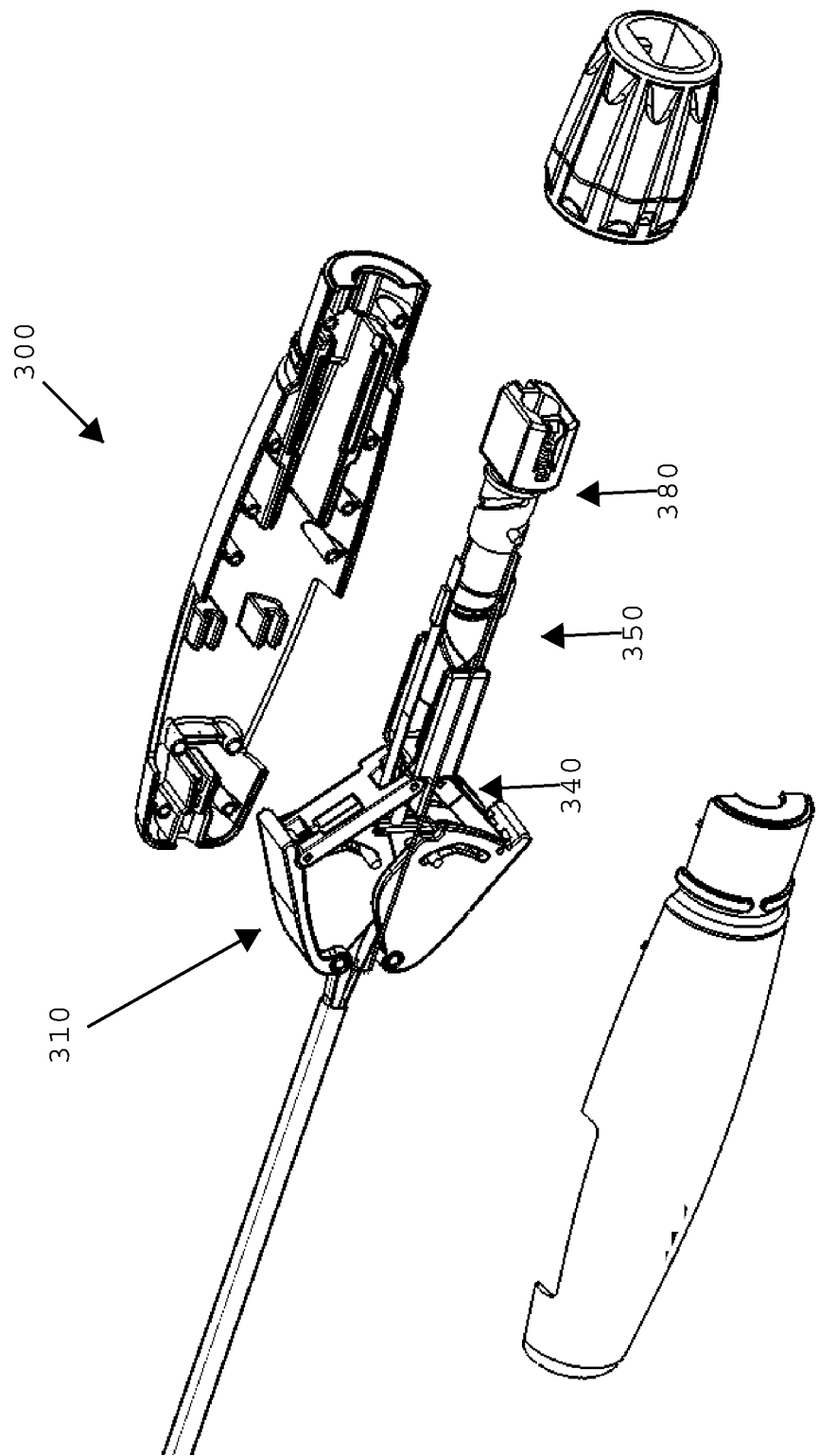
FIG. 42 is a partially exploded view of an embodiment of handle assembly of the suturing device of FIG. 41.
Figure 43:
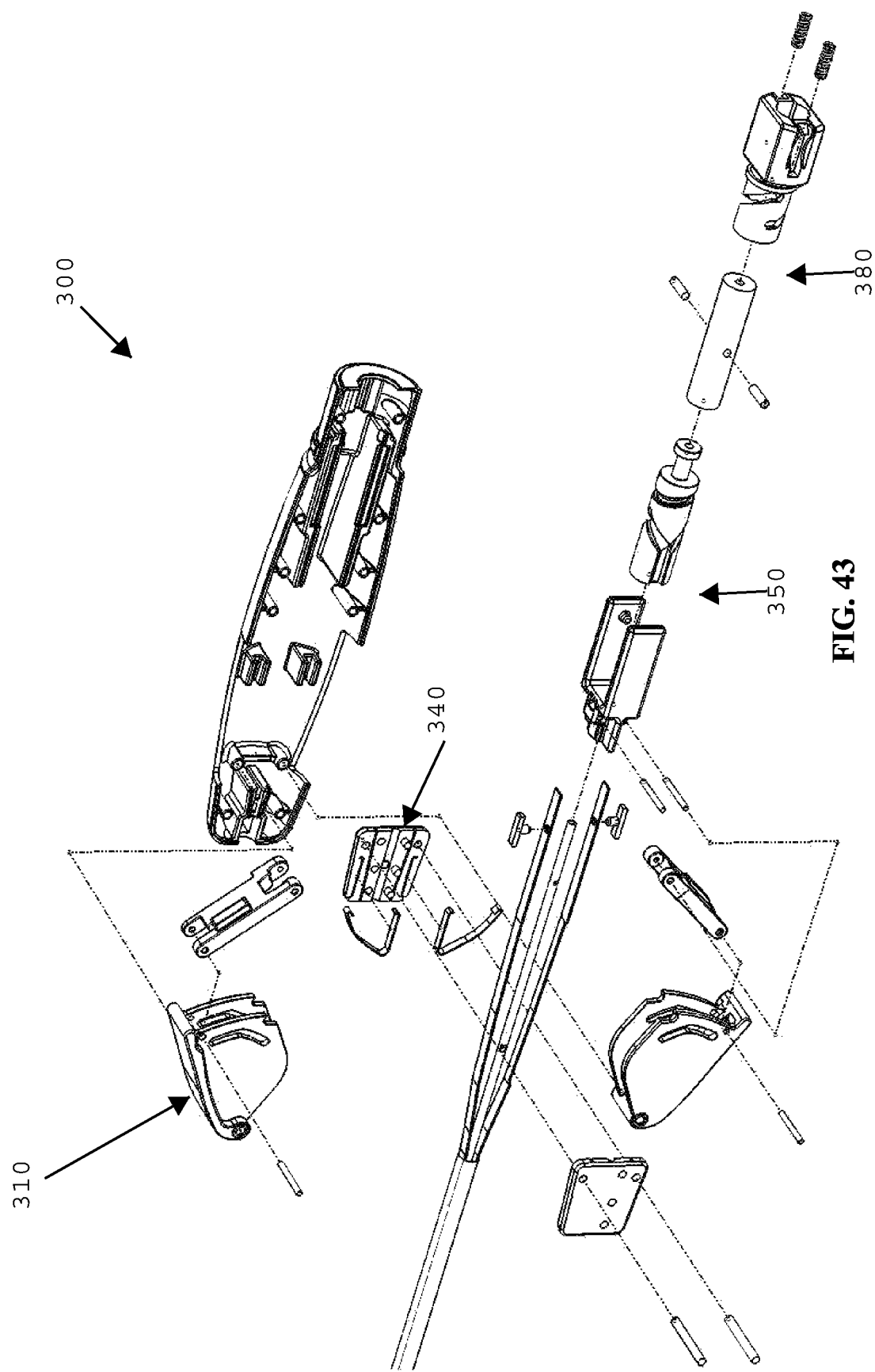
FIG. 43 is an exploded view of the handle assembly of FIG. 42.

With reference to FIGS. 42-43, an embodiment of handle assembly is illustrated in partially exploded and fully exploded view. In FIG. 42, a handle housing has been removed to illustrate a trigger mechanism 310, closure mechanism 340, toggle mechanism 350, and latch mechanism 380 therein. In FIG. 43, the trigger mechanism 310, closure mechanism 340, toggle mechanism 350, and latch mechanism 380 are illustrated in an exploded arrangement.

Figure 44:
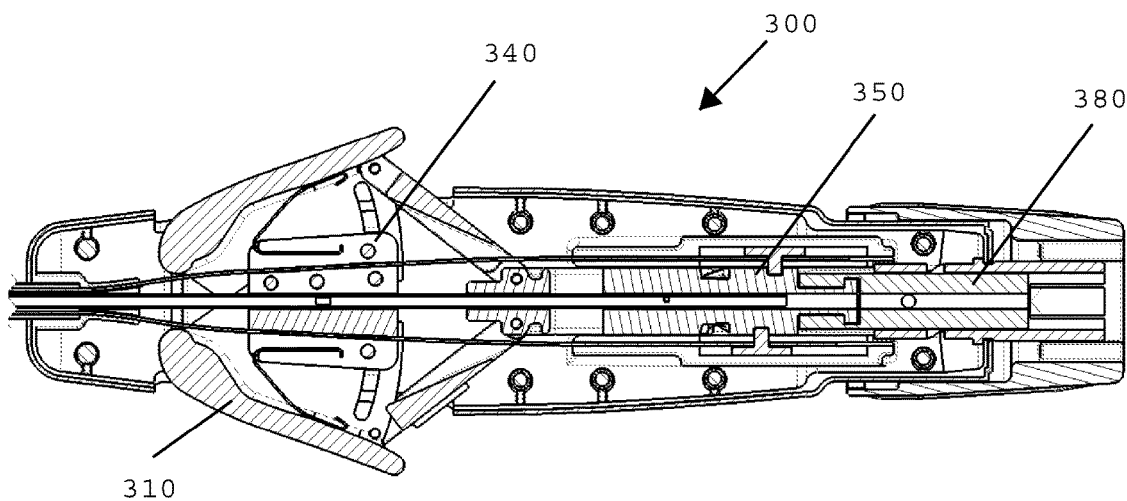
FIG. 44 is a cross sectional top view of the handle assembly of FIG. 42.
Figure 45:
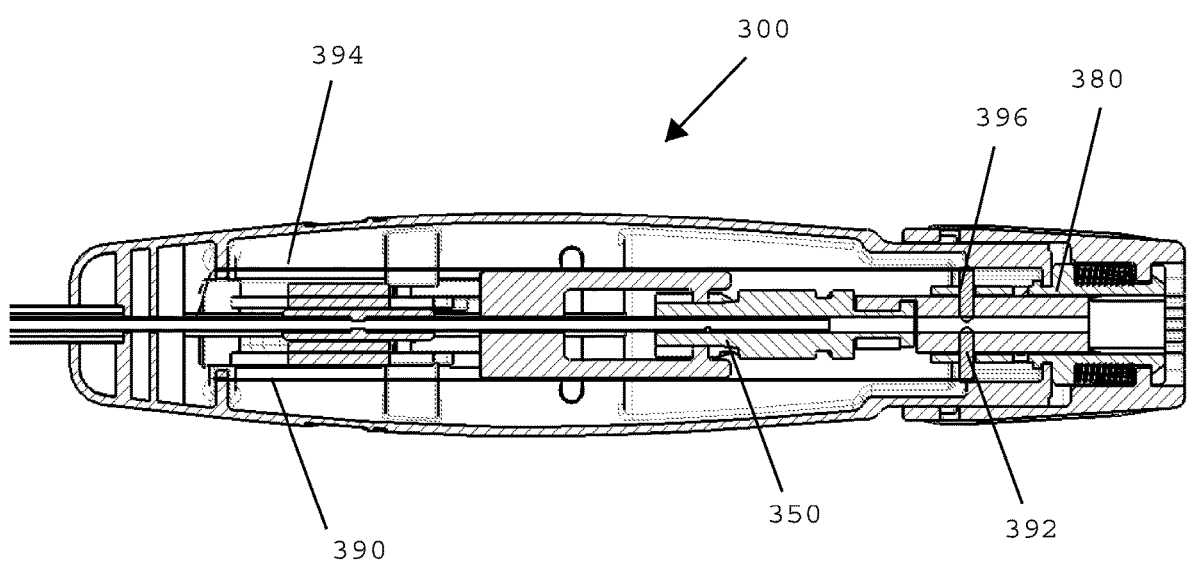
FIG. 45 is a cross sectional side view of the handle assembly of FIG. 42.

With reference to FIGS. 44-45, cross sectional views of an embodiment of handle assembly are illustrated. FIG. 44 illustrates a top cross sectional view. FIG. 45 illustrates a side cross sectional view.

Figure 46:
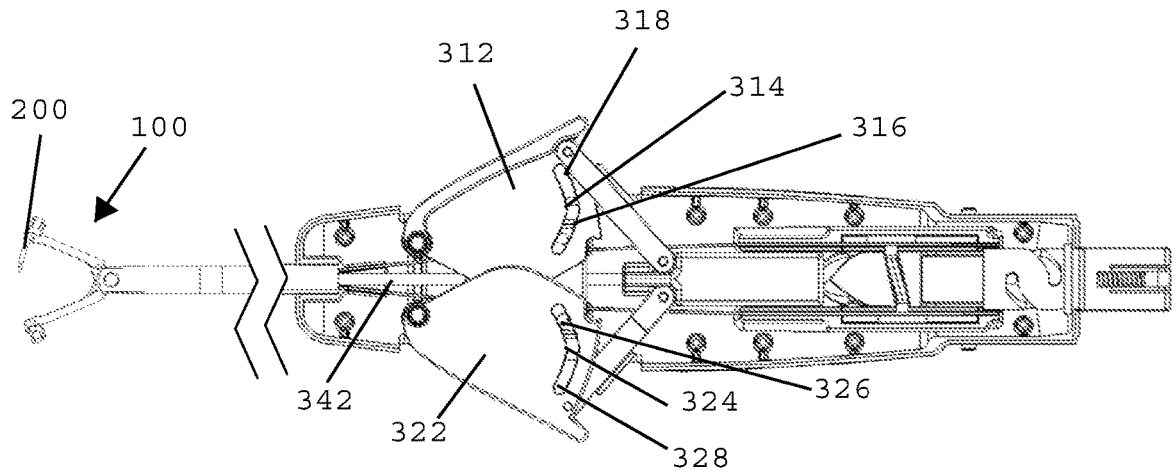
FIG. 46 is a partial cross sectional view of the suturing device of FIG. 41 in an open configuration with a top cross sectional view of the handle assembly.
Figure 47:
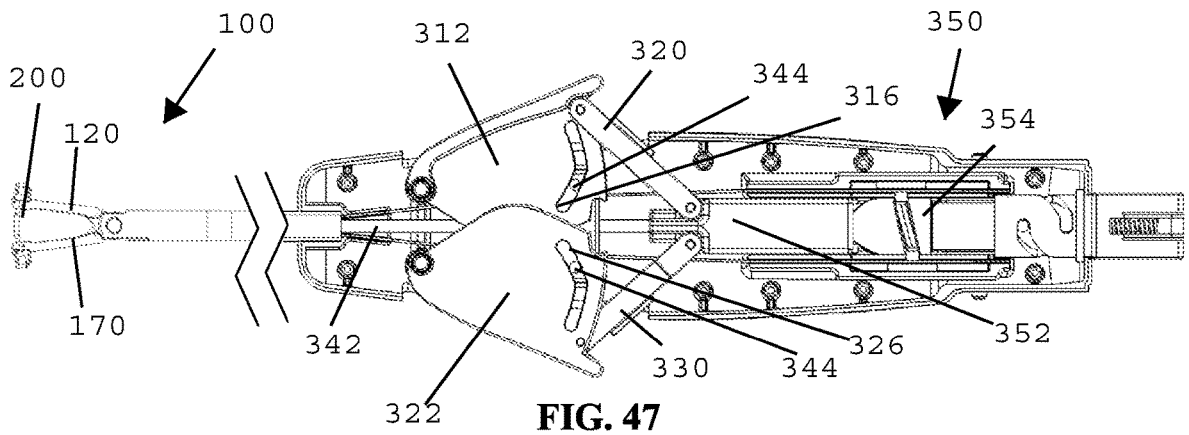
FIG. 47 is a partial cross sectional view of the suturing device of FIG. 41 in a partially-closed configuration with a top cross sectional view of the handle assembly.
Figure 48:
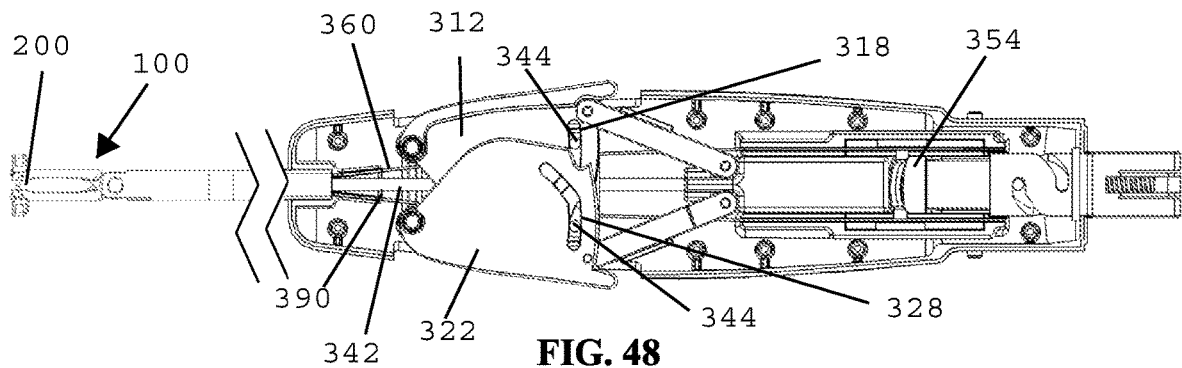
FIG. 48 is a partial cross sectional view of the suturing device of FIG. 41 in a closed configuration with a top cross sectional view of the handle assembly.
Figure 49:
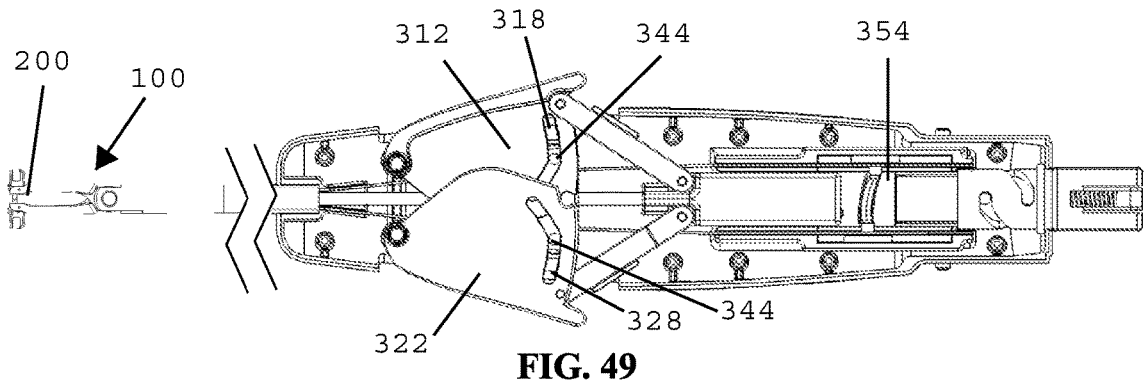
FIG. 49 is a partial cross sectional view of the suturing device of FIG. 41 in a closed configuration with a top cross sectional view of the handle assembly.
Figure 50:
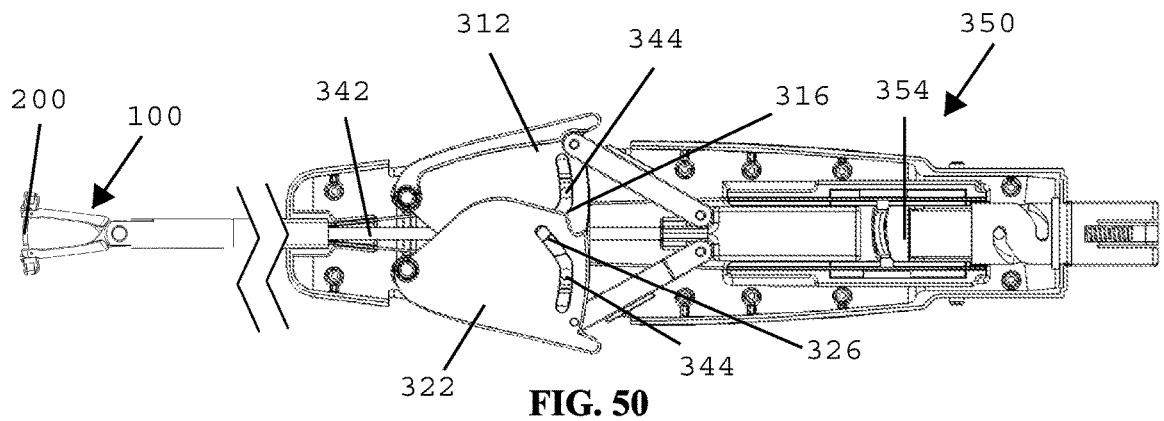
FIG. 50 is a partial cross sectional view of the suturing device of FIG. 41 in a partially closed configuration with a top cross sectional view of the handle assembly.
Figure 51:
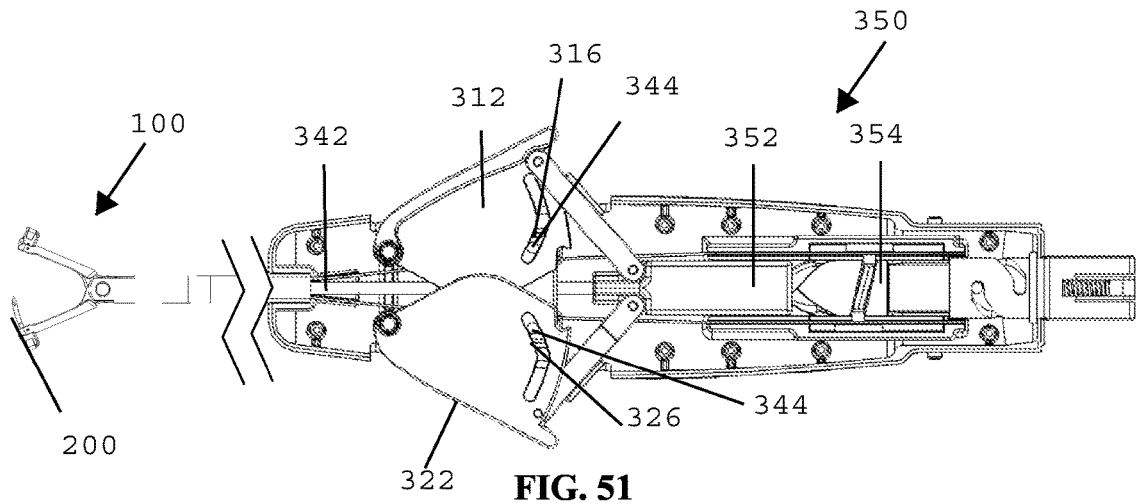
FIG. 51 is a partial cross sectional view of the suturing device of FIG. 41 in an open configuration with a top cross sectional view of the handle assembly.

With reference to FIGS. 46-51, partial cross-sectional views of the handle assembly are illustrated along with corresponding positions of the jaw assembly 100 and needle 200. FIG. 46 illustrates the handle assembly in an initial position with the needle 200 positioned in first jaw 110. FIGS. 47-48 illustrate an operational sequence as first and second levers 312, 322 of the trigger mechanism are squeezed towards the handle body of handle assembly 300. FIGS. 49-51 illustrate an operational sequence as first and second levers 312, 322 of the trigger mechanism 310 are released from the handle body of handle assembly 300.

With reference to FIGS. 46-48, the trigger mechanism can include a pair of opposed levers 312, 322 each pivotable with respect to the handle body. As illustrated, the levers can be pivotably coupled to the handle body adjacent a distal end of the handle assembly. Each of the levers 312, 322 can comprise a drive slot 314, 324 formed therein. As illustrated, the drive slots 314, 324 can include profiles configured to initially close the jaws as the levers are squeezed, then maintain closure upon further movement of the levers 312, 322 while the toggle mechanism is actuated. For example, the drive slots 314, 324 can include a driving segment 316, 326 and a dwell segment 318, 328. A closure mechanism 340 can include posts guided by the drive slots 314, 324 and coupled to a proximal end of the drive rod 342, which extends distally through elongate shaft 50 to the jaw actuation mechanism 150. Accordingly, upon initial movement of the levers 312, 322 toward handle body, (FIGS. 46-47), posts 344 are guided through driving segments 316, 326 of drive slots 314, 324 to longitudinally translate drive rod 342 and close base jaws 120, 170 (FIG. 47).

With reference to FIGS. 47-48, further compression of the levers 312, 322 towards handle body results in posts 344 of the closure mechanism moving in dwell segments 318, 328 of drive slots 314, 324, resulting in minimal further displacement of drive rod 342. However, the levers 312, 322 of trigger mechanism are each pivotally coupled to first ends of actuation links 320, 330 extending generally proximally within the handle assembly. Second ends of the actuation links 320, 330 opposite the first ends are coupled to a drive pusher 352 that is longitudinally translatable within the handle body. Longitudinal translation of the drive pusher 352 within the handle body can actuate the toggle mechanism 350 to selectively rotate a toggle tube 354 within the handle body as further described with reference to FIGS. 52-60.

With reference to FIGS. 46-48, an initial compression of the levers 312, 322 of trigger mechanism (FIGS. 46-47) actuates actuation links 320, 330 to translate the drive pusher 352 proximally along the toggle tube 354 of the toggle mechanism 350. Further compression of the levers 312, 322 of the trigger mechanism actuates actuation links 320, 330 to translate drive pusher proximally along the toggle tube 354 and rotate the toggle tube about a longitudinal axis of the handle body. As further described herein with reference to FIGS. 52-60, rotation of the toggle tube 354 alternately longitudinally advances one of the first shim 360 and the second shim 370 to retain the needle 200 alternately in one of the first and second jaws. Thus, when a user squeezes the levers 312, 322 of the trigger mechanism, the jaws of the jaw assembly are closed, and the needle 200 is passed from one jaw to another.

With reference to FIGS. 49-51, releasing the levers 312, 322 guides the posts 344 of the closure mechanism 340 along the dwell segments 318, 328 of the slots 314, 324 (FIGS. 49-50). During this initial opening movement, the toggle tube 354 continues to rotate, completing the advancement of one of the shims. As the levers continue to spread, the posts 344 of the closure mechanism 340 ride along the driving segments 316, 326 of the slots 314, 324 (FIGS. 50-51) such that the drive rod 342 is longitudinally translated to return the jaw assembly to an open configuration. This further movement translates the drive pusher 352 distally along toggle tube 354 of toggle mechanism 350.

Figure 52:
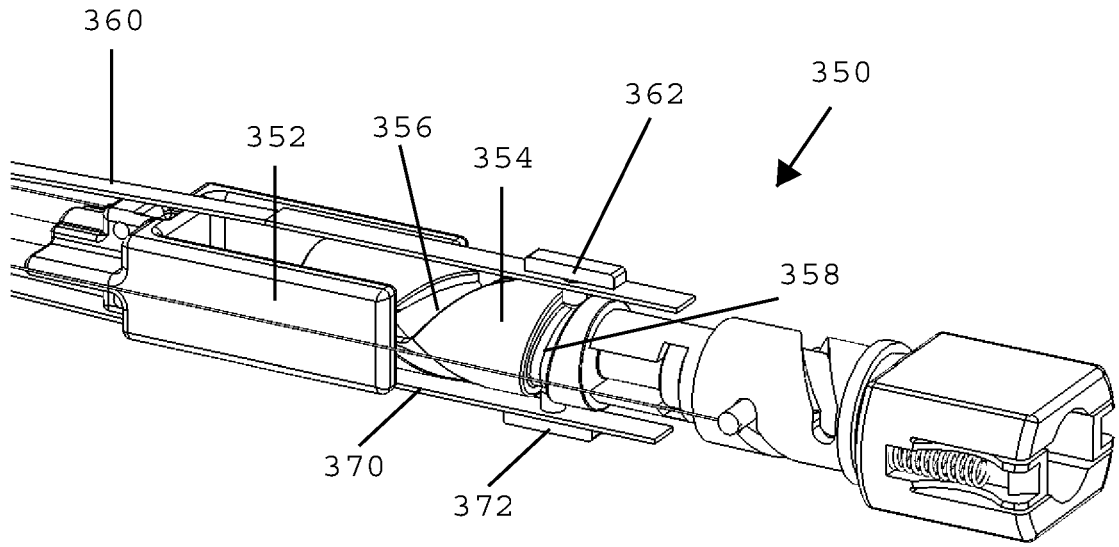
FIG. 52 is an isometric view of embodiments of toggling and latch mechanisms of the handle assembly of FIG. 41
Figure 53:
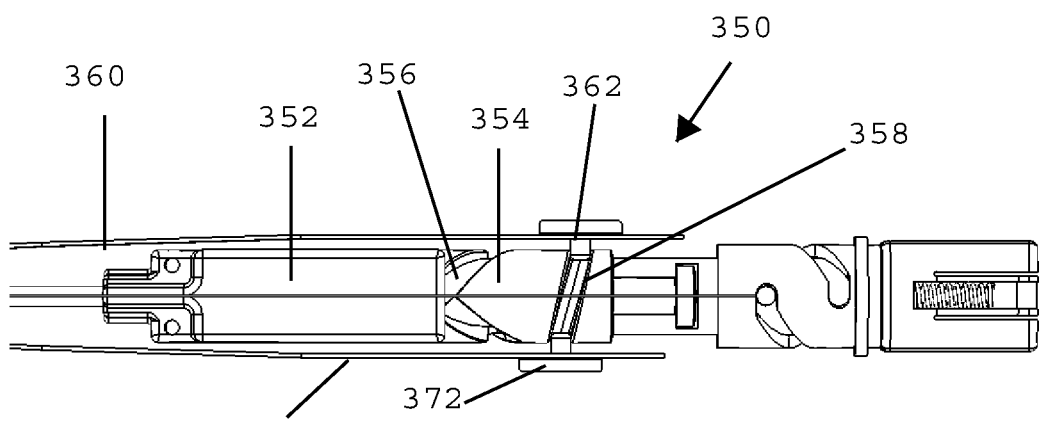
FIG. 53 is a side view of the toggling and latch mechanisms of FIG. 52.
Figure 54:
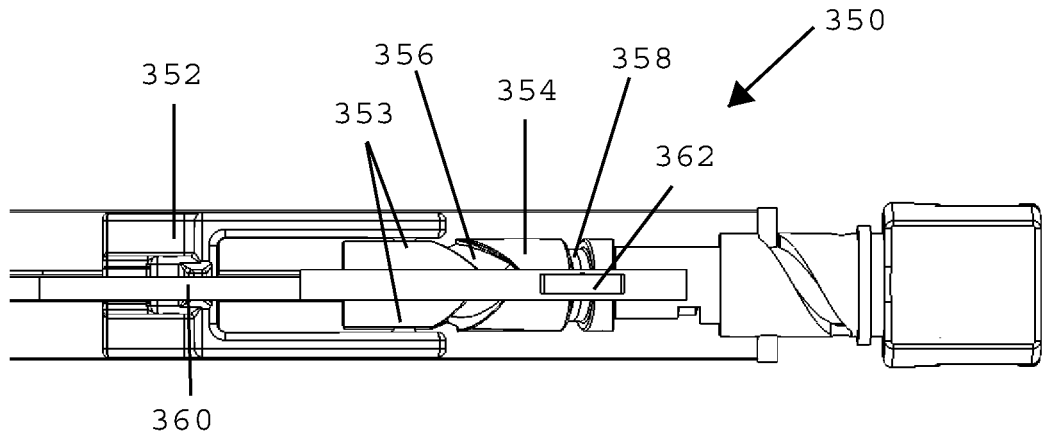
FIG. 54 is a top view of the toggling and latch mechanisms of FIG. 52.

With reference to FIGS. 52-54, various aspects of the toggle mechanism are illustrated in isometric, top, and side views. As illustrated, the toggle mechanism 350 comprises a drive pusher 352 longitudinally slideable within the handle body by actuation of the trigger mechanism 310. The drive pusher 352 can include a forked proximal end having a follower 353 such as a post protruding from each fork of the drive pusher 352. While the drive pusher 352 is illustrated as a monolithically formed component, in other embodiments, fork arms of the pusher could be discrete parts that function in a similar fashion. In some embodiments, the arms of the pusher can be rigid with a translating pin and spring element keeping the pin in contact with the toggle tube. The toggle mechanism 350 can also include a toggle tube 354 rotatable within the handle body. As illustrated, the toggle tube 354 comprises a cam drive slot 356 and a shim guide 358. The followers 353 of the drive pusher can be positioned in the cam drive slot 356. The cam drive slot 356 can include a pair of generally longitudinally extending lead segments and a rotation segment extending at an angle transverse to a longitudinal axis of the handle body between the lead segments.

With continued reference to FIGS. 52-54, the toggle mechanism 350 can further comprise a first shim 360 having a first follower 362 at a proximal end thereof and a second shim 370 having a second follower 372 at a proximal end thereof. The followers 362, 372 can comprise protruding posts extending radially inwardly from the shims 360, 370. Each of the followers 362, 372 can be positioned in the shim guide 358 of the toggle tube 354. In other embodiments, the shims can include radially inwardly extending flanges positioned in the shim guide to move the shims without followers. The shim guide 358 can have a shim advancement profile such that rotation of the toggle tube 354 within the handle body alternately longitudinally advances or retracts the followers 362, 372 of the shims 360, 370. Thus, rotation of the toggle tube 354 in a toggle cycle can alternately advance and retract the shims 360, 370 to alternately retain the needle within one or the other of the flip jaws as described with reference to FIGS. 18-20.

Figure 55:
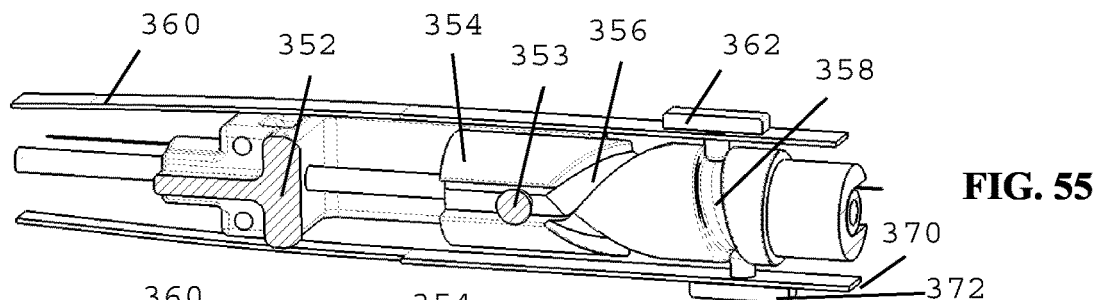
FIG. 55 is a section view of the toggling mechanism of FIG. 52 with a follower in a first position during a toggle cycle.
Figure 56:
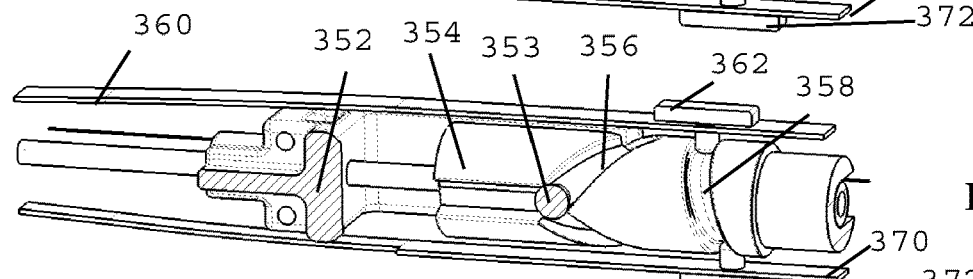
FIG. 56 is a section view of the toggling mechanism of FIG. 52 with a follower in a second position during a toggle cycle.

With reference to FIGS. 55-60, an operational sequence of the toggle mechanism is illustrated in sectional views. In FIG. 55, the follower 353 of the drive pusher 352 is positioned in the longitudinal lead segment of the cam drive slot 356, the first shim 360 is in a distally advanced position, and second shim 370 is in a retracted position. During an initial squeezing operation of the trigger mechanism, corresponding to closing the jaw assembly as described above with reference to FIGS. 46-47, the follower 353 is advanced longitudinally proximally along the lead segment of the cam drive slot 356, as illustrated in FIGS. 55-56. The toggle tube 354 is not rotated during this operation, and the first and second shims 360, 370 remain in their initial positions.

Figure 57:
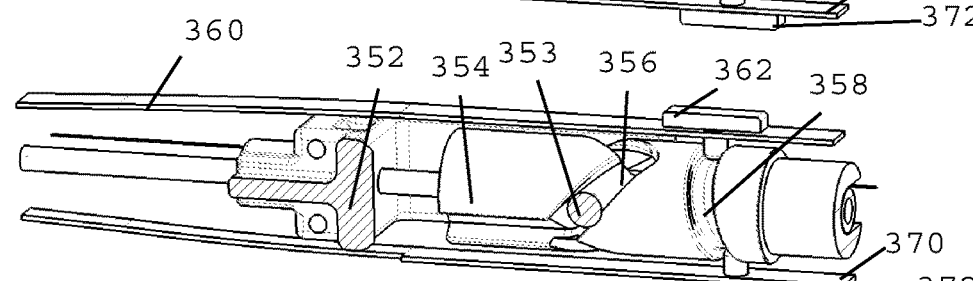
FIG. 57 is a section view of the toggling mechanism of FIG. 52 with a follower in a third position during a toggle cycle.
Figure 58:
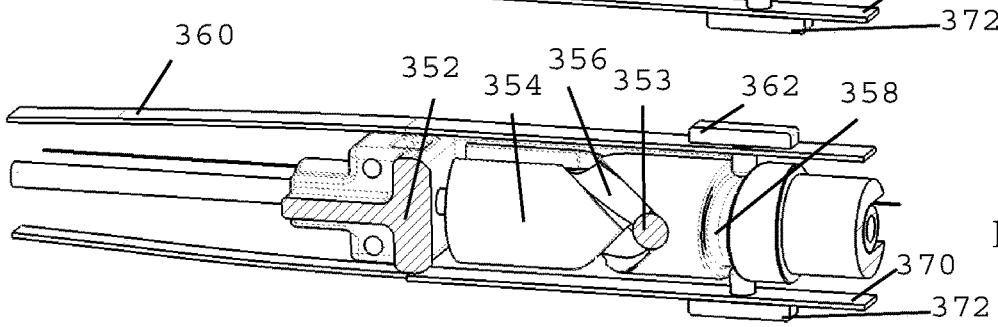
FIG. 58 is a section view of the toggling mechanism of FIG. 52 with a follower in a fourth position during a toggle cycle.

With reference to FIGS. 56-58, during the operational sequence of the toggle mechanism 350, once the trigger mechanism is squeezed beyond jaw closure (FIGS. 47-48), the follower 353 of the drive pusher 352 reaches the rotation segment of the cam drive slot 356. The rotation segment can be configured to rotate the toggle tube 354 a predetermined direction upon actuation by the drive pusher 352. For example, the rotation segment can have a variable depth profile at an intersection of the rotation segment with the lead segment such that as the follower 353 is advanced into rotation segment, it tends to follow a desired segment of the rotation segment to rotate the toggle tube a predetermined direction. The rotation segment extends along the toggle tube 354 transverse to a longitudinal axis of the handle body such that further proximal advancement of the drive pusher 352 and follower 353 relative to the toggle tube rotates the toggle tube 354 within the handle body (FIGS. 56-58). This rotation of the toggle tube 354 likewise rotates the shim guide 358 such that the first shim follower 362 and first shim 360 are withdrawn proximally while second shim follower 372 and second shim 370 are advanced distally. Thus, during a continued squeezing operation of the trigger mechanism, corresponding to closing the jaw assembly as described above with reference to FIGS. 47-48, the follower 353 is advanced along the rotation segment of the cam drive slot 356, as illustrated in FIGS. 56-58. The toggle tube 354 is rotated during this operation, and the first and second shims 360, 370 are longitudinally moved.

Figure 59:
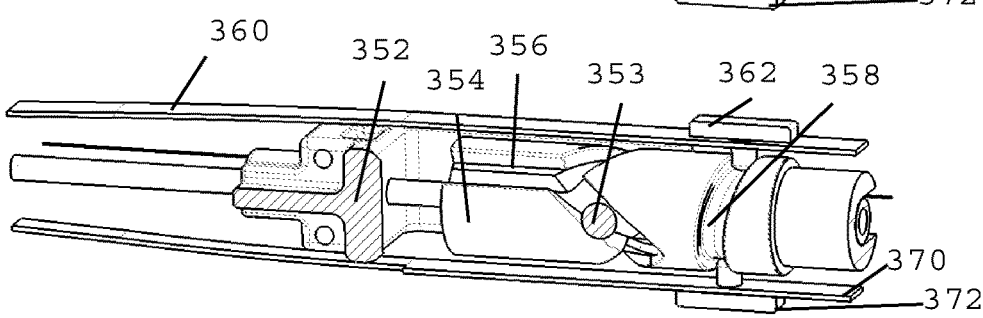
FIG. 59 is a section view of the toggling mechanism of FIG. 52 with a follower in a fifth position during a toggle cycle.
Figure 60:
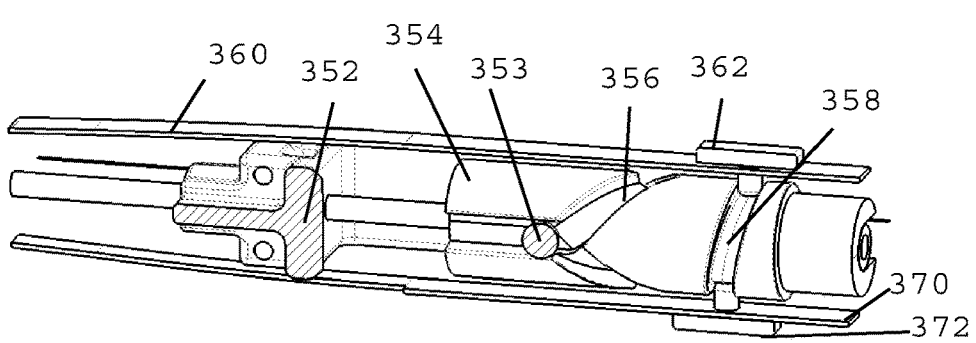
FIG. 60 is a section view of the toggling mechanism of FIG. 52 with a follower in a first position after a completed toggle cycle.

With reference to FIGS. 58-60, during the operational sequence of the toggle mechanism 350, once the trigger mechanism is released from a fully squeezed orientation (FIGS. 49-51), the follower 353 of the drive pusher 352 reaches a proximal-most peak of the rotation segment of the cam drive slot 356 (FIG. 58). The rotation segment can be configured to continue rotating the toggle tube 354 a predetermined direction upon release of the trigger mechanism and distal movement of the drive pusher 352. For example, the rotation segment can have a variable depth profile at the proximal-most peak of the rotation segment such that as the follower 353 is advanced along the rotation segment, it tends to follow a desired segment of the rotation segment to rotate the toggle tube a predetermined direction. Furthermore, the follower 353 can be disposed at an end of a flexible arm on the drive pusher, which acts as a leaf spring allowing the follower 353 to advance over a depth step. The rotation segment extends along the toggle tube 354 transverse to a longitudinal axis of the handle body such that initial distal withdrawal of the drive pusher 352 and follower 353 relative to the toggle tube continues to rotate the toggle tube 354 within the handle body (FIGS. 58-59). Advantageously, this continued rotation is provided by a "double action" stroke of the toggle tube (i.e. rotation during both squeezing and releasing the trigger mechanism). This double action stroke desirably halves the stroke length of the trigger mechanism that would otherwise be required to rotate the toggle tube and allows for a lower pressure angle of the follower 353 and cam drive slot 356 system. This rotation of the toggle tube 354 likewise rotates the shim guide 358 such that the first shim follower 362 and first shim 360 are withdrawn proximally while second shim follower 372 and second shim 370 are advanced distally. Thus, during an initial release operation of the trigger mechanism, corresponding to the initial dwell portion as described above with reference to FIGS. 49-50, the follower 353 is advanced along the rotation segment of the cam drive slot 356, as illustrated in FIGS. 58-59. The toggle tube 354 is rotated during this operation, and the first and second shims 360, 370 continue to move longitudinally until the second shim 370 reaches a distally advanced position and the first shim reaches a proximally withdrawn position.

With reference to FIG. 60, during the operational sequence of the toggle mechanism 350, as the trigger mechanism continues to travel to a fully released position (FIGS. 50-51), the follower 353 of the drive pusher 352 reaches the longitudinal lead segment of the cam drive slot 356 (FIG. 60). The rotation segment can have a variable depth profile at the intersection of the rotation segment with the lead segment such that as the follower 353 is withdrawn proximally, it tends to enter the lead segment. Thus continued distal withdrawal of the drive pusher 352 and follower 353 relative to the toggle tube along the longitudinally-extending lead segment maintains the rotational orientation of the toggle tube 354 within the handle body (FIG. 60). Thus, during a fully released operation of the trigger mechanism, corresponding to the jaw opening portion as described above with reference to FIGS. 50-51, the follower 353 is advanced along the lead segment of the cam drive slot 356, as illustrated in FIG. 60. During this operation, the second shim 370 remains in the distally advanced position and the first shim 360 remains in the proximally withdrawn position.

Accordingly, in the illustrated embodiment, one compress and release cycle of the trigger mechanism cycles the toggle mechanism 350 to rotate the toggle tube 354 180 degrees. This rotation of the toggle tube 354 180 degrees repositions one shim 360 from a distally advanced position to a proximally withdrawn position and repositions the other shim 370 from a proximally withdrawn position to a distally advanced position. Thus, advantageously, the illustrated toggle mechanism can allow a single trigger mechanism to actuate both a jaw open/close/open cycle and alternately advance a shim to retain a needle in one of the jaws. In other embodiments, other toggle mechanisms can be used to alternately advance and withdraw shims responsive to a cycle of a trigger mechanism.

As discussed above, the flip jaws utilize a torsion spring and cable mechanism for rotation between the stowed and suturing configurations. The flip jaws rotate about a dowel pin that is held on either end of the flip jaw by the base jaw. In some embodiments, a distal end of the cable is welded to the bottom of a corresponding flip jaw and is controlled by a latch mechanism in the handle. In other embodiments, the cables can be attached to corresponding flip jaws by crimping each cable into a slot in the corresponding flip jaw, or having a fitting on the end of each cable that attaches to the corresponding flip jaw. In other embodiments, the flip jaw cable can also be fixed to the flip jaw by solder or brazing. The torsion spring is on the flip jaw's rotation axis, between the flip jaw and base jaw. The spring is biased to rotate the flip jaw into the activated, suturing configuration. To rotate the flip jaws to the activated state, the tension in the cable is released to allow the torsion springs to flip the jaws. To rotate the flip jaws into the deactivated state, the cable is tensioned.

Figure 61:
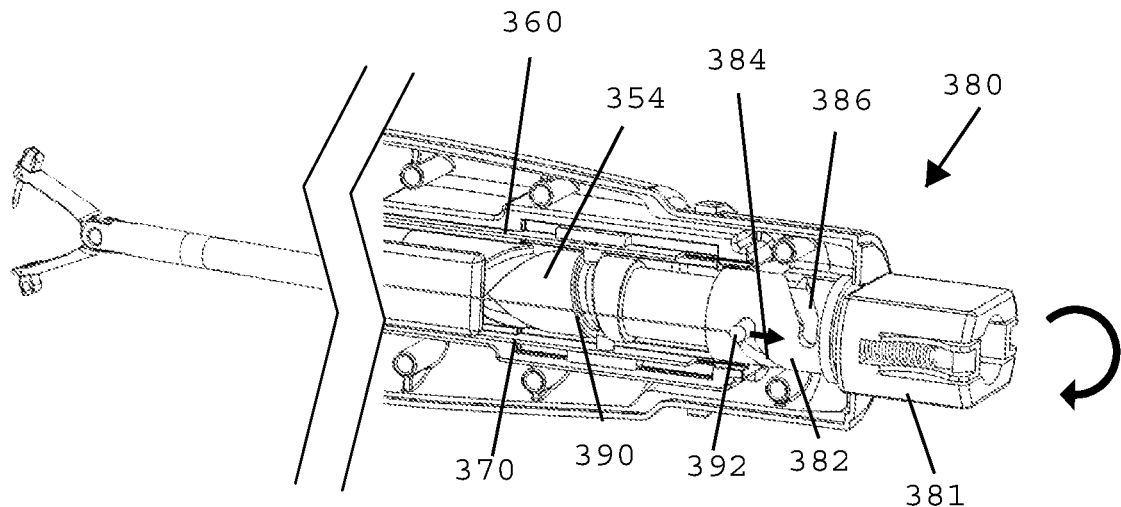
FIG. 61 is a partial cross sectional view of the suturing device of FIG. 41 in an open configuration with a side cross sectional view of the handle assembly.
Figure 62:
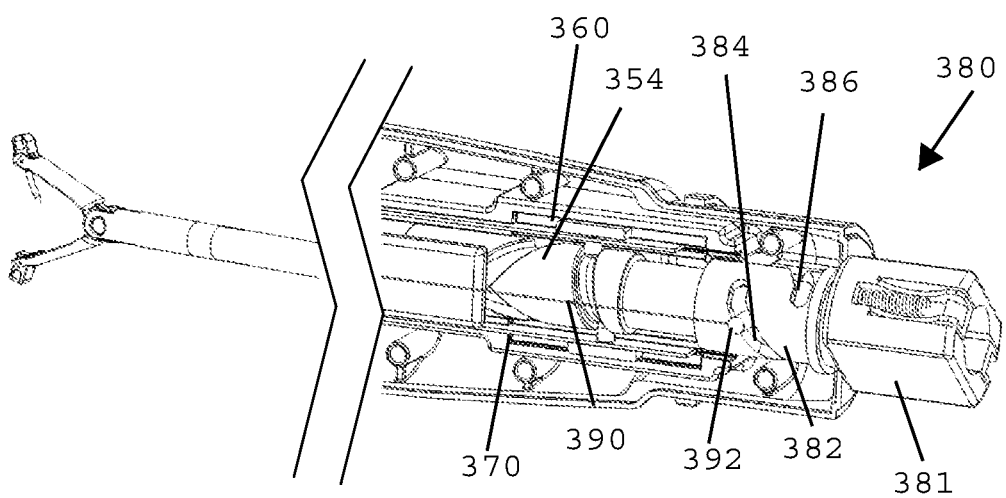
FIG. 62 is a partial cross sectional view of the suturing device of FIG. 41 with flip jaws rotated by the latch mechanism to a partially stowed configuration with a side cross sectional view of the handle assembly.
Figure 63:
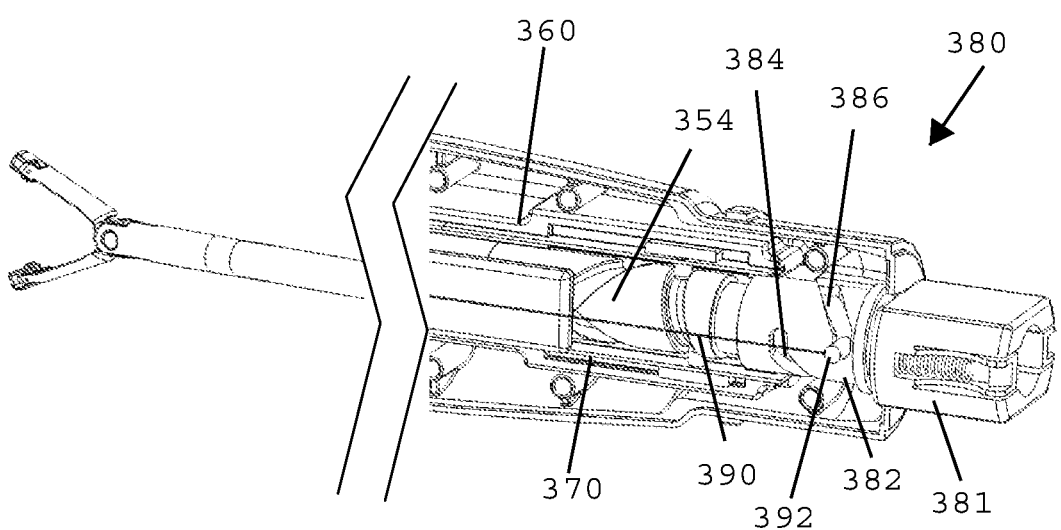
FIG. 63 is a partial cross sectional view of the suturing device of FIG. 41 with flip jaws rotated by the latch mechanism to a stowed configuration with a side cross sectional view of the handle assembly.

With reference to FIG. 61-63, an operational sequence of the latch mechanism 380 is illustrated. FIG. 61 illustrates the latch mechanism in an unlatched configuration corresponding to a suturing configuration of the flip jaws. The latch mechanism 380 can comprise a latch knob 381 at a proximal end of the handle assembly. In the illustrated embodiment, the latch knob 381 is coupled to a latch tube 382 having first and second guide slots 384, 386 formed therein. The latch mechanism further comprises first and second cables 390, 394 extending distally through the handle assembly and elongate shaft and coupled to the flip jaws of the jaw assembly as described above with respect to FIGS. 14-17. Proximal ends of the cables 390, 394 are coupled to posts 392, 396 positioned within the guide slots 384, 386 of the latch tube 382. The posts 392, 396 can be dowel pins protruding from a bearing tube that is coupled to the toggle tube 354 of the toggle mechanism such that proximal movement of the posts 392, 296 withdraws the toggle tube and shims 360, 370 proximally.

With continued reference to FIGS. 61-63, upon rotation of the latch knob 381, latch tube 382 correspondingly rotates. Thus, posts 392, 396 are withdrawn proximally by interaction with guide slots 384, 386 of guide tube. This proximal movement of posts 392, 396 applies tension to cables 390, 394 to pivot flip jaws from the suturing configuration (FIG. 61) to the stowed configuration (FIG. 63). This proximal movement of posts 392, 396 also withdraws toggle tube 354 and shims 360, 370 proximally. With the latch mechanism 380 partially rotated, the shims 360, 370 can be withdrawn from both jaws such that the jaw assembly can be reloaded with a new needle, if desired. Further rotation of the latch knob 381 positions the posts 392, 396 at an end of the guide slots 384, 386 that can be configured, such as with a flat segment or detent, to maintain the latch mechanism 380 in a latched configuration having the flip jaws in the stowed configuration.

When it is desired to unlatch the device to position the flip jaws in the suturing configuration, the sequence of FIGS. 61-63 can be performed in reverse. In the unlatching sequence, the latch mechanism in the handle both releases the cable tension and also slides the needle locking shims forward in one motion. After the cable tension is released and the springs finish rotating the flip jaws to the activated state, the shims then slide forward into the flip jaws to prevent them from rotating back into the deactivated state. One shim will slide further in order to lock the needle in that jaw. In some embodiments, the latch mechanism can further comprise a tensioning spring to maintain tension in the cables in both the latched and unlatched configurations of the suturing device.

While a torsion spring biased unlatching and cable driven latching operation of the latching mechanism is illustrated, it is contemplated that in other embodiments, other latching mechanisms can be used with suturing devices as described herein. For example, in some embodiments, each jaw can include a first cable to pivot the flip jaw to a suturing configuration and a second cable to pivot the flip jaw to a stowed configuration. In other embodiments, the flip jaws can be rotated or pushed into the suturing or stowed configurations using a more rigid cable or rod that can both push and pull the flip jaw, eliminating the need for a torsion spring or two counteracting cables. In still other embodiments, the flip jaws can be pivoted relative to the base jaws by a worm gear and sector, Nitinol actuators, or a lead screw and nut device.

Figure 64:
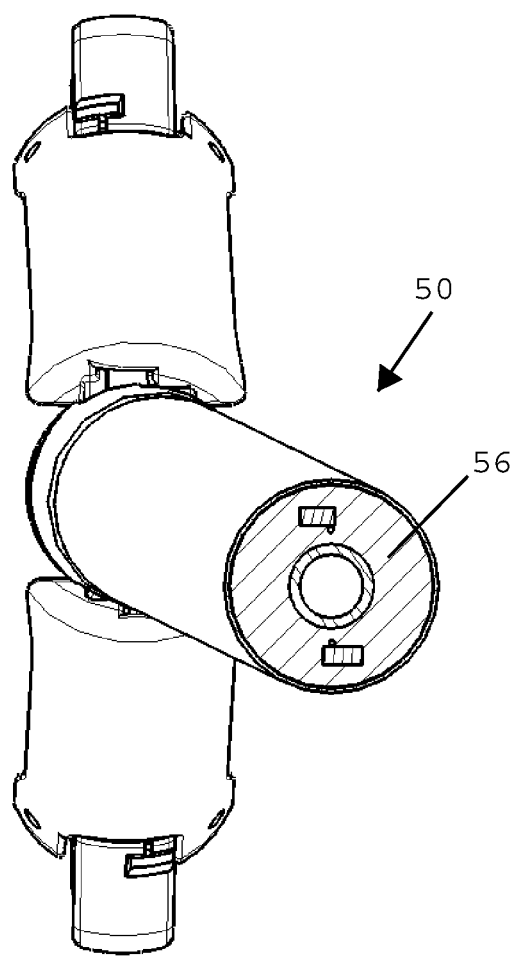
FIG. 64 is a cross sectional view of an embodiment of elongate shaft of the suturing device of FIG. 41.

With reference to FIG. 64, a cross section of the elongate shaft adjacent the distal end is illustrated. In the illustrated embodiment, the elongate shaft 50 can include a cover tube and a spacer member 56 through which the drive rod, cables, and shims extend. In some embodiments, the spacer member can be an extruded member. The spacer member can prevent buckling of the shims, cables, and drive rod inside the cover tube. When the user squeezes the levers of the trigger mechanism, the levers transmit the force to the drive rod down the length of the device's shaft.

Figure 65:
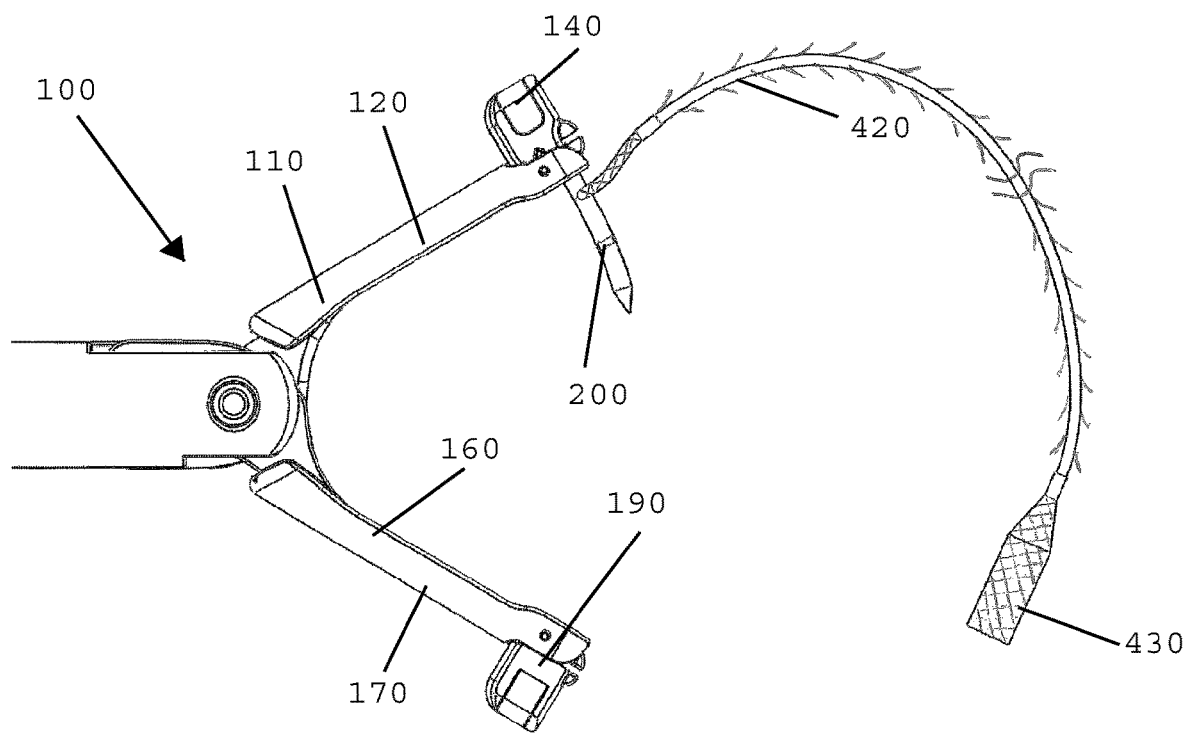
FIG. 65 is a side view of an embodiment of the jaw assembly of a suturing device having a needle with a barbed suture and a braided anchor.
Figure 66:
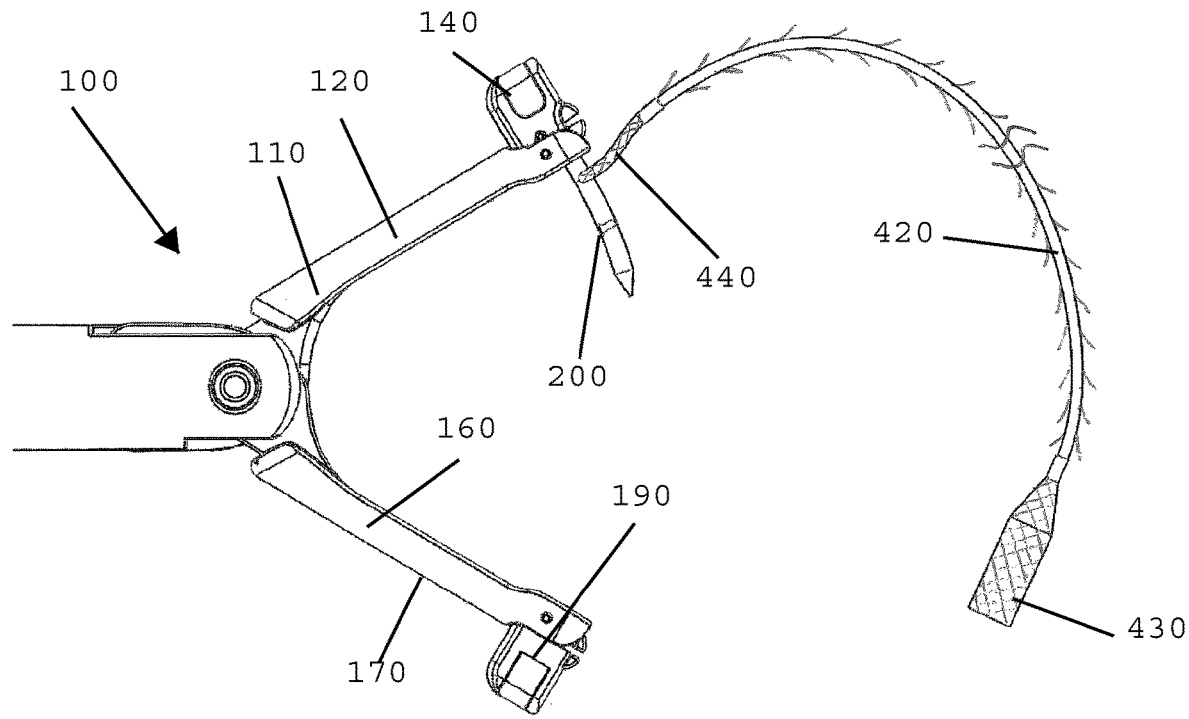
FIG. 66 is a side view of an embodiment of the jaw assembly of a suturing device having a needle with a barbed suture, a braided leader, and a braided anchor.

With reference to FIGS. 65 and 66, in some embodiments, the needle 200 and suture 420 can include a braided polymeric tube anchor 430. The braided polymer tube 430 can be disposed at an end of the suture opposite the needle for use as an anchor for the suture. The braided polymer tube 430 anchor can be attached to the end of the suture via welding, adhesive, or another joining method. Advantageously, the braided polymer tube 430, with multiple insertion areas provided by voids between adjacent areas of overlapping polymer strands, can provide for a relatively easy target for a surgeon to thread the needle through.

With reference to FIG. 66, in certain embodiments, the needle 200 and suture 420 can include a leader segment 440 comprising a braided polymer tube between the needle 200 and the suture 420. The braided polymeric tube can allow for enhanced flexibility of the suture at the needle interface.

With reference to FIGS. 65 and 66, in certain embodiments, the needle and suture 420 can include a unidirectional barbed suture to facilitate retention of tissue by the suture. In other embodiments, a smooth monofilament suture can be used with a braided polymer tube anchor and/or braided polymer tube leader.

Suturing devices described herein can incorporate various materials and combinations of materials in their construction. For example, in some embodiments, the flip jaws, base jaws, clevis, slotted head, drive rod, cables, torsion springs, shims, dowel pins, needle, detent spring, detent ball, cover tube, suture crimp, toggle tube, and rivet can be made of metals such as stainless steel, aluminum, titanium, tungsten, brass, bronze, or alloys of such. In some embodiments, the shims and/or cables can be made out of Nickel-Titanium (Nitinol) to allow greater flexibility and fatigue life. In some embodiments, the monofilament or braided suture and flexible multifilament leader can be made of non-bioabsorbable polymers such as polypropylene, nylon, polyester, or silk, or from bioabsorbable polymers such as polydioxanone, polylactic acid, polyglycolide, polylactic-co-glycolic acid, polycaprolactone, or catgut. In some embodiments some or all of the trigger levers, linkages, latch, knob, shim followers, and drive rod adapters can be made of plastics such as polycarbonate, ABS, polyethylene, polypropylene, PEEK, polyurethane, PVC, acrylic, nylon, polystyrene, acetal, carbon fiber, polyimide, or polyester.

While the illustrated embodiments of suturing device include a latching mechanism to configure jaws to a stowed, low diametric profile configuration for insertion of a relatively large needle through a relatively low diameter surgical port, it is contemplated that in other embodiments of suturing device, other configurations can achieve a low diametric profile for insertion. For example, in some embodiments, a suturing device can include a telescopically compressible needle. A compression element such as a spring can be contained in the needle and enable two halves of the needle to concentrically compress when subjected to forces greater than tissue puncturing. The closure of the jaws can be selectively controlled by the handle with one setting for passage of the needle from jaw to jaw and another setting to enable further closure of the jaws to compress the needle to the low profile state to enable withdrawal through a 5 mm trocar.

In the illustrated embodiment, the suture is positioned along the elongate shaft with the jaw assembly in a low-profile stowed configuration for insertion through a surgical port. It is contemplated that in other embodiments, the profile of the suturing device can be further reduced for insertion. For example, in some embodiments, the clevis and outer tube of the elongate shaft can have an axial groove formed therein for the suture to align in during insertion through a trocar, reducing the cross sectional profile of the device. In other embodiments, suture can be coiled or folded within the two base jaws during insertion through the trocar in order to reduce the cross sectional profile of the device. The base jaws can be closed around the coiled or folded suture with the jaw assembly in the stowed state. The base jaws can then be opened while inside the body cavity to release the suture. In other embodiments, the suturing device can further comprise an introducing tube in which the suture may be coiled or folded for insertion through the trocar. This introducing tube can desirably reduce the cross sectional profile of the device during insertion through a trocar and allow the use of larger profile suture anchors. The introducing tube can cover the base jaws while they are fully closed in the stowed configuration. Once inserted into the body cavity, another instrument such as a surgical grasper can pull the introducing tube off the jaws, releasing the suture inside the body cavity. The introducing tube can then be immediately removed from the body cavity through the other instrument's trocar.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A laparoscopic suturing device comprising:
    a handle assembly having a proximal end and a distal end, the handle assembly comprising a trigger, a drive rod, and a toggle tube;
    an elongate shaft extending distally from the distal end of the handle assembly and defining a central longitudinal axis;
    a jaw assembly extending distally from the elongate shaft, the jaw assembly comprising a first jaw and a second jaw each having a proximal end pivotably coupled to the elongate shaft and a distal end; and
    a needle;

wherein the trigger is operably coupled to the drive rod and the toggle tube such that an actuation cycle of the trigger sequentially actuates the drive rod to close the first jaw and the second jaw of the jaw assembly, actuates the toggle tube to transfer the needle from one of the first jaw and the second jaw to the other of the first jaw and the second jaw, and actuates the drive rod to open the first jaw and the second jaw.

2. The laparoscopic suturing device of claim 1, wherein the drive rod extends longitudinally through the elongate shaft, the drive rod having a proximal end coupled to the trigger.

3. The laparoscopic suturing device of claim 2, wherein the trigger comprises a drive slot formed therein and the drive rod comprises a post positioned in the drive slot coupling the drive rod to the trigger.

4. The laparoscopic suturing device of claim 3, wherein the drive slot comprises a profile having a driving segment arranged to translate the drive rod upon actuation of the trigger and a dwell segment arranged to maintain position of the drive rod upon further actuation of the trigger.

5. The laparoscopic suturing device of claim 1, wherein the trigger is coupled to an actuation link having an end coupled to a drive pusher longitudinally translatable within the handle assembly.

6. The laparoscopic suturing device of claim 5, wherein the toggle tube is rotatable with respect to the handle assembly about the central longitudinal axis, the toggle tube comprising a cam drive slot and a shim guide formed therein.

7. The laparoscopic suturing device of claim 6, wherein the drive pusher is coupled to the cam drive slot such that translation of the drive pusher within the handle assembly rotates the toggle tube with respect to the handle assembly.

8. The laparoscopic suturing device of claim 6, further comprising a first shim and a second shim each coupled to the shim guide of the toggle tube such that rotation of the toggle tube alternately longitudinally advances and retracts the first shim and the second shim relative to the handle assembly.

9. A laparoscopic suturing device comprising:
a handle assembly comprising a handle body having a proximal end and a distal end, the handle assembly comprising a trigger mechanism, a closure mechanism, and a toggle mechanism;
an elongate shaft extending distally from the distal end of the handle assembly and defining a central longitudinal axis;
an end effector assembly having a first jaw and a second jaw; and
a needle;
wherein the trigger mechanism comprises a pair of opposed levers each pivotable with respect to the handle body, each of the levers comprising a drive slot formed therein; and
wherein the closure mechanism comprises:
  a plurality of posts each guided by a corresponding drive slot; and
  a drive rod having a proximal end and extending distally from the proximal end the elongate shaft to the end effector assembly, the plurality of posts coupled to the proximal end of the drive rod to operably couple the trigger mechanism to the closure mechanism;
wherein the trigger mechanism is operably coupled to the closure mechanism and the toggle mechanism such that an actuation cycle of the trigger mechanism sequentially actuates the closure mechanism and the toggle mechanism;
wherein each of the opposed levers is pivotably coupled to the handle body adjacent a distal end of the handle assembly;
wherein each of the opposed levers extends from a first end pivotably coupled to the handle body at the distal end of the handle assembly to a second end, and further comprising a plurality of actuation links each extending between a first end and a second end, the first end of each actuation link coupled to the second end of a corresponding one of the opposed levers;
wherein the second ends of the actuation links are each coupled to a drive pusher longitudinally translatable within the handle body; and
wherein the toggle mechanism comprises a toggle tube rotatable within the handle body and wherein longitudinal translation of the drive pusher selectively rotates the toggle tube.

10. A laparoscopic suturing device comprising:
a handle assembly comprising a handle body having a proximal end and a distal end, the handle assembly comprising a trigger mechanism, a closure mechanism, and a toggle mechanism;
an elongate shaft extending distally from the distal end of the handle assembly and defining a central longitudinal axis;
an end effector assembly having a first jaw and a second jaw; and
a needle;
wherein the trigger mechanism comprises a pair of opposed levers each pivotable with respect to the handle body, each of the levers comprising a drive slot formed therein; and
wherein the closure mechanism comprises:
  a plurality of posts each guided by a corresponding drive slot; and
  a drive rod having a proximal end and extending distally from the proximal end the elongate shaft to the end effector assembly, the plurality of posts coupled to the proximal end of the drive rod to operably couple the trigger mechanism to the closure mechanism;
wherein each of the opposed levers is pivotably coupled to the handle body adjacent a distal end of the handle assembly;
wherein each of the opposed levers extends from a first end pivotably coupled to the handle body at the distal end of the handle assembly to a second end, and further comprising a plurality of actuation links each extending between a first end and a second end, the first end of each actuation link coupled to the second end of a corresponding one of the opposed levers;
wherein the second ends of the actuation links are each coupled to a drive pusher longitudinally translatable within the handle body; and
wherein the toggle mechanism comprises a toggle tube rotatable within the handle body and wherein longitudinal translation of the drive pusher selectively rotates the toggle tube.

11. The laparoscopic suturing device of claim 10, wherein each of the drive slots comprises a driving segment and a dwell segment.

12. The laparoscopic suturing device of claim 11, wherein upon initial movement of the opposed levers towards the handle body, the plurality of posts are guided through the corresponding driving segments to longitudinally advance the drive rod.

13. The laparoscopic suturing device of claim 12, wherein upon further movement of the opposed levers, the plurality of posts are guided through the corresponding dwell segments to minimally further displace the drive rod.

* * * * *